US009289925B2

(12) United States Patent
Ferguson et al.

(10) Patent No.: US 9,289,925 B2
(45) Date of Patent: Mar. 22, 2016

(54) METHODS OF MAKING HOLLOW MICRONEEDLE ARRAYS AND ARTICLES AND USES THEREFROM

(75) Inventors: Dennis E. Ferguson, Mahtomedi, MN (US); Stanley Rendon, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1198 days.

(21) Appl. No.: 13/262,996

(22) PCT Filed: Mar. 22, 2010

(86) PCT No.: PCT/US2010/028095
§ 371 (c)(1),
(2), (4) Date: Oct. 5, 2011

(87) PCT Pub. No.: WO2010/117602
PCT Pub. Date: Oct. 14, 2010

(65) Prior Publication Data
US 2012/0041337 A1 Feb. 16, 2012

Related U.S. Application Data

(60) Provisional application No. 61/168,268, filed on Apr. 10, 2009.

(51) Int. Cl.
*B29C 43/02* (2006.01)
*B29C 33/30* (2006.01)
*A61M 37/00* (2006.01)
*B29C 33/00* (2006.01)

(52) U.S. Cl.
CPC .......... *B29C 43/021* (2013.01); *A61M 37/0015* (2013.01); *B29C 33/301* (2013.01); *A61M 2037/003* (2013.01); *A61M 2037/0053* (2013.01); *B29C 33/0088* (2013.01); *B29C 2043/025* (2013.01)

(58) Field of Classification Search
CPC .. B29C 33/0088; B29C 33/301; B29C 33/302
See application file for complete search history.

(56) References Cited

U.S. PATENT DOCUMENTS 3,649,153 A * 3/1972 Brudy ................... B29C 33/302
249/117
3,833,699 A * 9/1974 Stefanka ............... B29C 33/302
264/314

(Continued)

FOREIGN PATENT DOCUMENTS

WO WO 2005/009645 2/2005
WO WO 2005/087305 9/2005

(Continued)

OTHER PUBLICATIONS

Perennes, F. et al., "Sharp Beveled Tip Hollow Microneedle Arrays Fabricated by LIGA and 3D Soft Lithography with Polyvinyl Alcohol," Journal of Micromechanics and Microengineering, vol. 16, (2006) p. 473-479.

(Continued)

*Primary Examiner* — Benjamin Schiffman
(74) *Attorney, Agent, or Firm* — Julie Lapos-Kuchar

(57) ABSTRACT

A method of making hollow microneedle arrays is described. Also described are the articles therefrom and the use of the articles in applications such as delivering fluid to and/or extracting body fluid from a subject.

13 Claims, 10 Drawing Sheets

(56) References Cited

U.S. PATENT DOCUMENTS

| | | | | |
|---|---|---|---|---|
| 3,914,101 | A | * | 10/1975 | Stefanka ............... B29C 33/302 264/507 |
| 4,066,236 | A | * | 1/1978 | Lindner ............... B29C 33/302 249/160 |
| 5,124,108 | A | | 6/1992 | Bennett et al. |
| 5,217,728 | A | * | 6/1993 | Grabbe ............... B29C 33/302 249/64 |
| 5,922,222 | A | | 7/1999 | Jens et al. |
| 6,010,609 | A | * | 1/2000 | Mimura ............... B29C 33/302 205/70 |
| 6,120,280 | A | * | 9/2000 | Mimura ............... B29C 33/302 249/104 |
| 6,213,753 | B1 | * | 4/2001 | Grabbe ............... B29C 33/302 425/192 R |
| 6,224,807 | B1 | | 5/2001 | Clune |
| 6,305,924 | B1 | | 10/2001 | Krinke et al. |
| 6,312,612 | B1 | | 11/2001 | Sherman et al. |
| 6,334,856 | B1 | | 1/2002 | Allen et al. |
| 6,471,893 | B1 | * | 10/2002 | Hsu ............... B29C 33/302 264/1.9 |
| 6,511,463 | B1 | | 1/2003 | Wood et al. |
| 6,533,981 | B1 | | 3/2003 | Jens et al. |
| 6,749,792 | B2 | | 6/2004 | Olson |
| 8,522,407 | B2 | * | 9/2013 | Mahe ............... A44B 18/0049 24/452 |
| 2006/0030812 | A1 | | 2/2006 | Golubovic-Liakopoulos et al. |
| 2006/0115621 | A1 | * | 6/2006 | Yang ............... A44B 18/0049 428/100 |
| 2007/0191761 | A1 | | 8/2007 | Boone et al. |
| 2008/0275400 | A1 | * | 11/2008 | Ferguson ............... A61M 37/0015 604/173 |
| 2009/0106955 | A1 | * | 4/2009 | Mahe ............... A44B 18/0049 24/452 |
| 2010/0305516 | A1 | * | 12/2010 | Xu ............... A61M 37/0015 604/272 |
| 2012/0041337 | A1 | * | 2/2012 | Ferguson ............... A61M 37/0015 600/573 |
| 2013/0344191 | A1 | * | 12/2013 | Mahe ............... A44B 18/0049 425/468 |

FOREIGN PATENT DOCUMENTS

| | | |
|---|---|---|
| WO | WO 2005082596 | 9/2005 |
| WO | WO 2006/062974 | 6/2006 |
| WO | WO 2006/135794 | 12/2006 |
| WO | WO 2007/075806 | 7/2007 |
| WO | WO 2007/080427 | 7/2007 |
| WO | WO 2007/112309 | 10/2007 |
| WO | WO 2007/124393 | 11/2007 |
| WO | WO 2007/127976 | 11/2007 |
| WO | WO 2008/027011 | 3/2008 |

OTHER PUBLICATIONS

PCT International Search Report, PCT/US2010/028095, mailed Dec. 6, 2010, 4 pages.

* cited by examiner

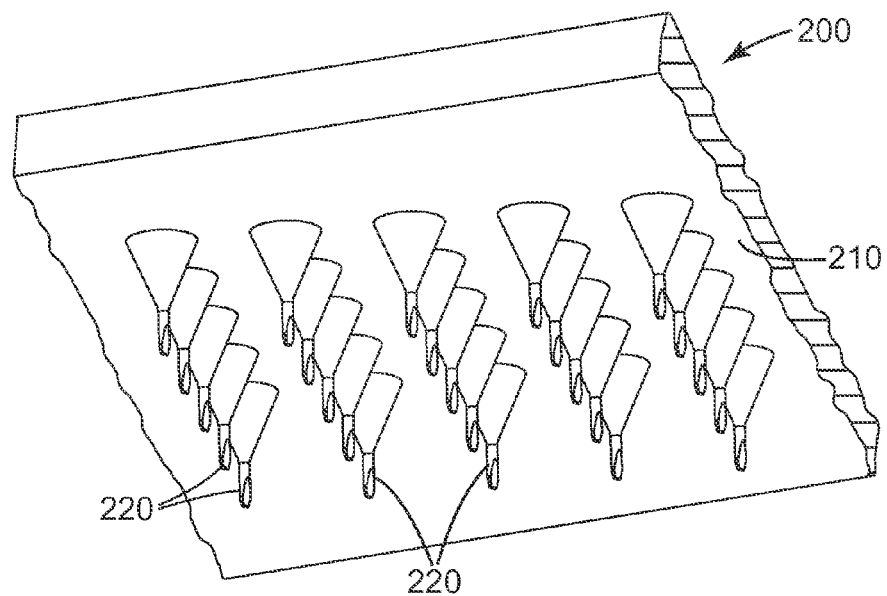
Fig. 2
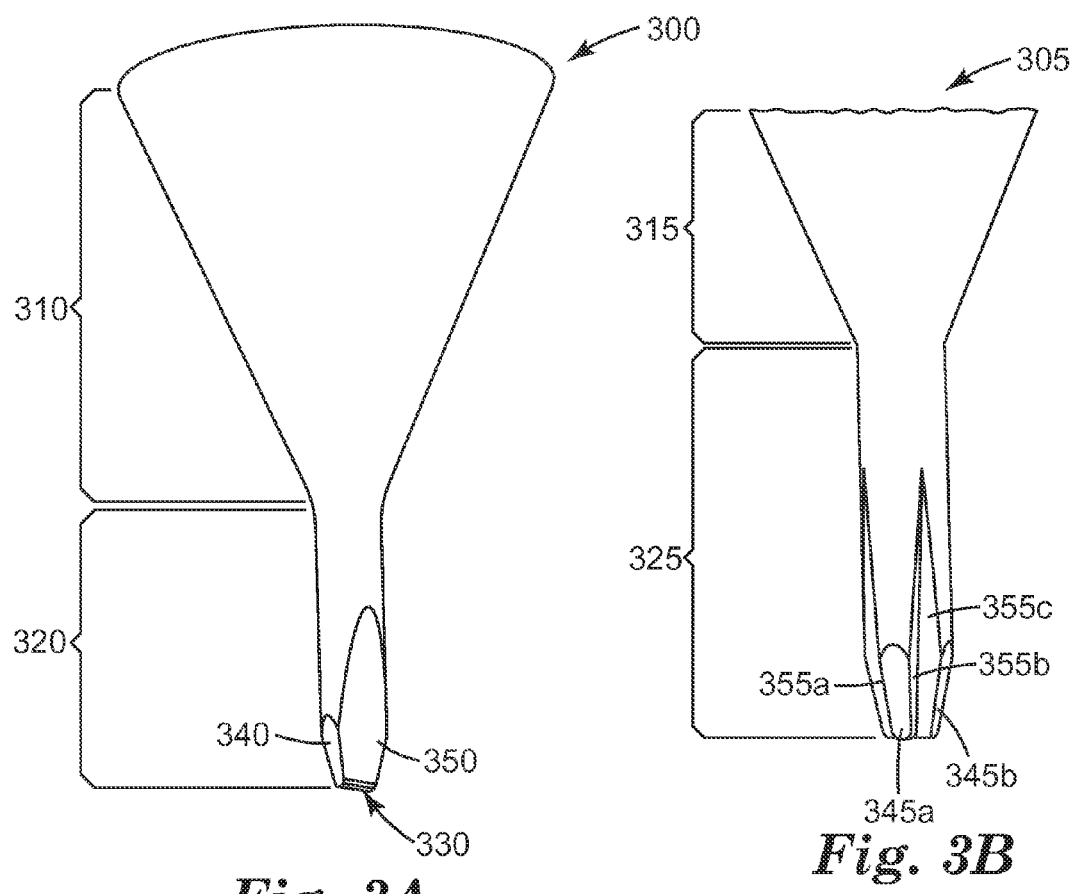
Fig. 3A
Fig. 3B

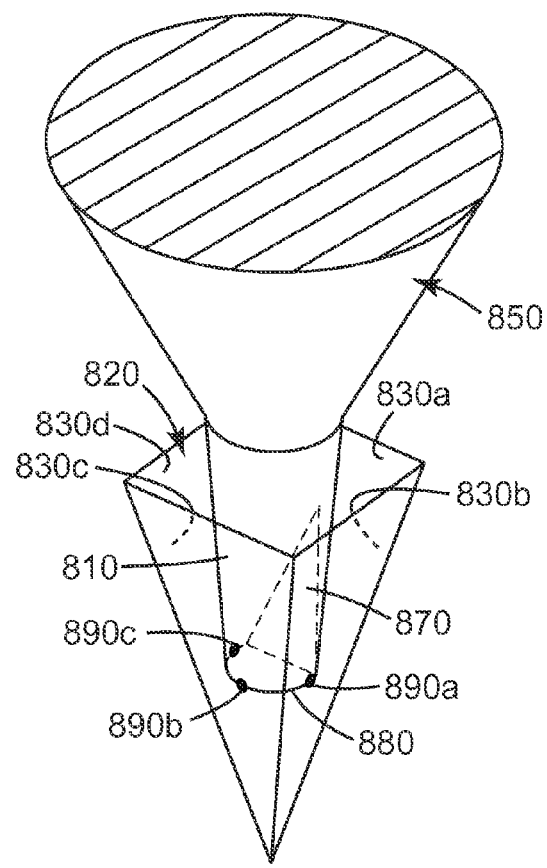
Fig. 8A
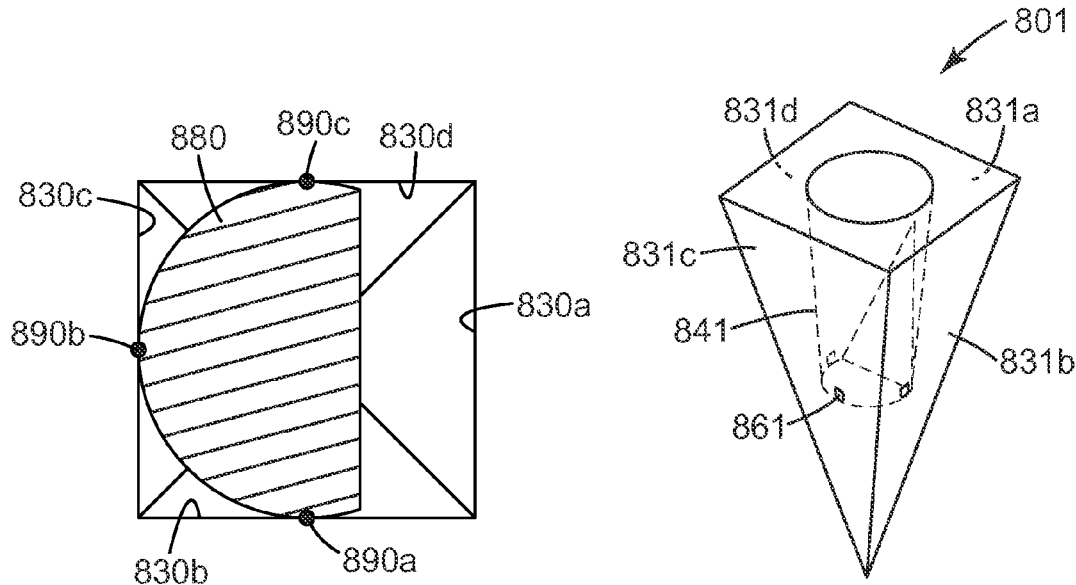
Fig. 8B
Fig. 8C

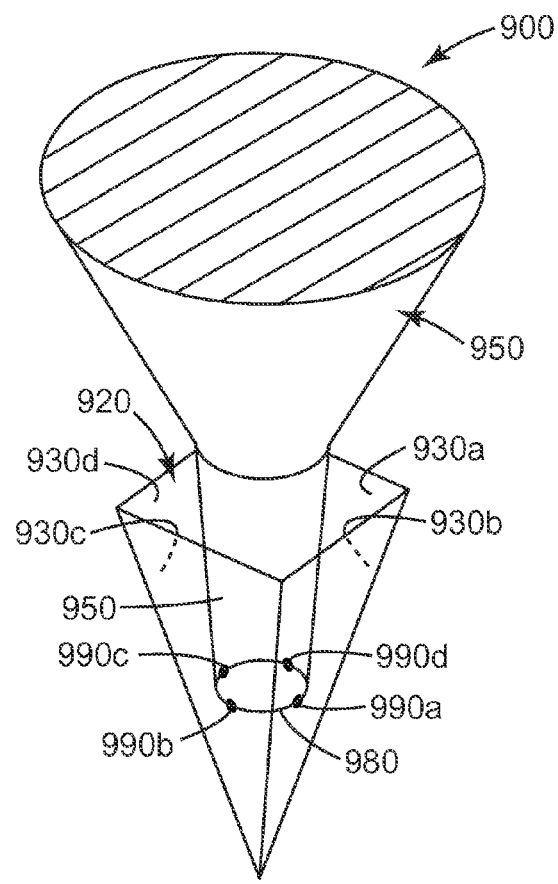
Fig. 9A
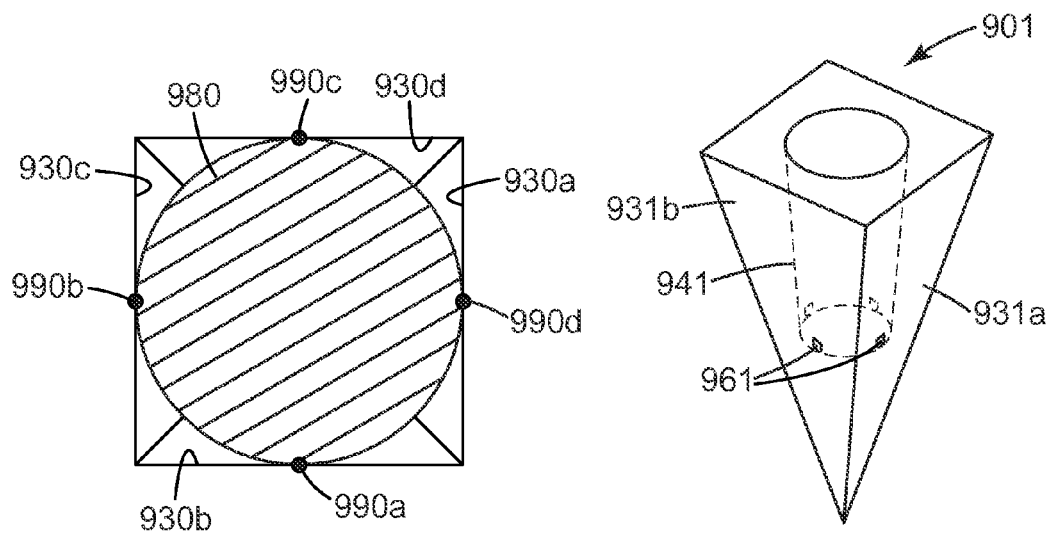
Fig. 9B
Fig. 9C

METHODS OF MAKING HOLLOW MICRONEEDLE ARRAYS AND ARTICLES AND USES THEREFROM

CROSS REFERENCE TO RELATED APPLICATIONS

This application is a national stage filing under 35 U.S.C. 371 of PCT/US2010/028095, filed Mar. 22, 2010, which claims priority to U.S. Provisional Application No. 61/168,268, filed Apr. 10, 2009, the disclosure of which is incorporated by reference in its/their entirety herein.

TECHNICAL FIELD

This disclosure broadly relates to methods of making hollow microneedle arrays and to articles therefrom.

BACKGROUND

Only a limited number of molecules with demonstrated therapeutic value can be transported through the skin, even with the use of approved chemical enhancers. The main barrier to transport of molecules through the skin is the stratum corneum (the outermost layer of the skin).

Devices including arrays of relatively small structures are sometimes referred to as microneedles, microneedle arrays, micro arrays, micro-pins, or the like. These structures have been disclosed for use in connection with the delivery of therapeutic agents and other substances through the skin and other surfaces. These medical devices pierce the stratum corneum and form a plurality of microscopic slits or holes in the outermost layer of skin to facilitate the transdermal delivery of therapeutic agents through the skin. The devices are typically pressed or abraded against the skin in an effort to pierce the stratum corneum such that the therapeutic agents and other substances can pass through that layer and into the tissues below.

In some embodiments, the microneedle arrays include structures that have a capillary or passageway extending through the microneedle. This capillary or passageway enables the microneedle to deliver fluid therapeutic agents through the skin of a subject or to extract fluids through the skin from the subject.

SUMMARY

Because the microneedle structures are small, the passageways (or capillaries) formed in the microneedles are limited in size. As a result, microneedles and the passageways of the microneedles can be difficult to manufacture. Further, microneedles having fine structural details with discrete microreplicated features anchored to a much larger macroscopic molded structure can be difficult to prepare in a polymeric molding process. The present inventors have determined that known microneedle molding processes all have certain disadvantages, which relate primarily to their inability to attain extremely precise feature replication at a commercial scale given their inherent limitations with air evacuation during molding.

There is a need for accurately determining and positioning the location of the passageways within the microneedles. The present inventors recognize a need for a method of manufacture for a high fidelity (i.e., replication that results in an article with near identical shape to its original cavity shape), low cycle time, high volume (i.e., molds can be used repeatedly), and contaminate-free net-shape hollow microneedle array.

In one aspect, the present disclosure provides a method of manufacturing a hollow microneedle array comprising: (a) providing a first mold half comprising a stacked laminate mold, the stacked laminate mold comprising a plurality of plates and a plurality of cavities, wherein each of the plates comprises: (i) opposed first and second major surfaces; and (ii) a first mold surface connecting said first and second major surfaces, and wherein the plurality of cavities is open at least to the first mold surface and includes a cavity surface wherein the cavity surface intersects each respective plate's first major surface and each respective plate's first mold surface. The method further comprises (b) providing a second mold half comprising a second mold surface, wherein the second mold surface comprises a plurality of projections; (c) contacting at least the first mold surface or the second mold surface with polymeric material; and (d) inserting the plurality of projections into the plurality of cavities.

In one embodiment, a method of manufacturing the hollow microneedle array is disclosed wherein the tip end of the projection contacts at least one surface of the cavity.

In another embodiment, a method of manufacturing the hollow microneedle array is disclosed wherein the plurality of cavities is vented by submicrometer spacing between the plurality of plates.

In another embodiment, a method of manufacturing the hollow microneedle array is disclosed wherein the cavity surface comprises a first material and the projection comprises a second material, wherein the first material has a specific strength that is at least 0.5 GPa (giga Pascal) higher than the specific strength of the second material.

In another aspect, a hollow microneedle array is disclosed made by any of the methods described herein. For instance, a hollow microneedle array may be made by (a) providing a first mold half comprising a stacked laminate mold, the stacked laminate mold comprising a plurality of plates and a plurality of cavities, wherein each of the plates comprises: (i) opposed first and second major surfaces; and (ii) a first mold surface connecting said first and second major surfaces; and wherein the plurality of cavities is open at least to the first mold surface and includes a cavity surface wherein the cavity surface intersects each respective plate's first major surface and each respective plate's first mold surface; (b) providing a second mold half comprising a second mold surface, wherein the second mold surface comprises a plurality of projections; (c) contacting at least the first mold surface or the second mold surface with polymeric material; and (d) inserting the plurality of projections into the plurality of cavities.

In yet another aspect, a use of the hollow microneedle array is described for injecting and/or extracting fluid.

The features and advantages of the present disclosure will be understood upon consideration of the detailed description of the preferred embodiment as well as the appended claims. These and other features and advantages of the disclosure may be described below in connection with various illustrative embodiments of the disclosure. The above summary of the present disclosure is not intended to describe each disclosed embodiment or every implementation of the present disclosure. The figures and the detailed description which follow more particularly exemplify illustrative embodiments.

BRIEF DESCRIPTION OF DRAWINGS

FIG. 2 is an isometric view of second mold half 200 according to one exemplary embodiment of the present disclosure.

FIG. 3A is an isometric view of projection 300 according to one exemplary embodiment of the present disclosure; and FIG. 3B is an isometric view of projection 305 according to one exemplary embodiment of the present disclosure.

FIG. 8A is an isometric view of projection 850 positioned inside of cavity 820 according to one exemplary embodiment of the present disclosure;

FIG. 8B is a cross-sectional plane of FIG. 8A taken at tip end 880, according to one exemplary embodiment of the present disclosure; and FIG. 8C is an isometric view of hollow microneedle 801 resulting from the cavity and projection of FIGS. 8A and 8B.

FIG. 9A is an isometric top-view of projection 950 positioned inside of cavity 920 according to one exemplary embodiment of the present disclosure;

FIG. 9B is a cross-sectional plane of FIG. 9A taken at tip end 980, according to one exemplary embodiment of the present disclosure; and FIG. 9C is an isometric view of hollow microneedle 901 resulting from the cavity and projection of FIGS. 9A and 9B.

While the above-identified drawing figures set forth several embodiments of the disclosure, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale.

DETAILED DESCRIPTION

Advantageously, the molding process of the present disclosure may offer the ability to reproduce the mold shape in the resulting molded article reliably, produce microneedles of a consistent height, produce microneedles with a submicrometer tip diameter, and produce hollow microneedle arrays in an economical fashion.

In the present application, the resulting molded article is referred to as a hollow microneedle array and is referred to in its use as a therapeutic device, however, the present disclosure should not be unduly limited to hollow microneedle arrays. Other microstructure articles are contemplated following the methods and procedures of the present disclosure, such as, for example, cylindrical posts, microelectronic devices, electrical connectors, medical microfluidic devices, fuel atomizers, and optoelectronic devices.

Figure 1A:
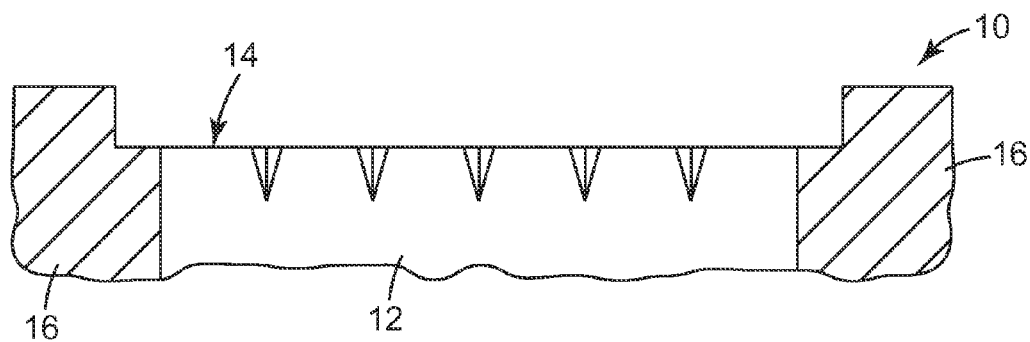
FIG. 1A is schematic side-view of first mold half 10 according to one exemplary embodiment of the present disclosure.

FIG. 1A depicts a side-view of one embodiment of a first mold half of the present disclosure. First mold half 10 comprises a stacked laminate mold 12 inserted between frame 16. First mold surface 14 has a structured surface and is a negative mold for the first major surface (patient- or subject-facing side) of the resulting molded article (e.g., the hollow microneedle array). Frame 16 may be used to secure the plates of stack laminate mold 12 together such that each plate is in intimate contact with an adjacent plate. The plates of are held together in intimate contact via physical or chemical means including, for example, clamping, bonding, or wedge blocking to form stacked laminate mold 12 and held in frame 16. For example, the frame may comprise crossbars to secure the plates of the stacked laminate, or holes to secure the plates of the stacked laminate to a base.

Figure 1B:
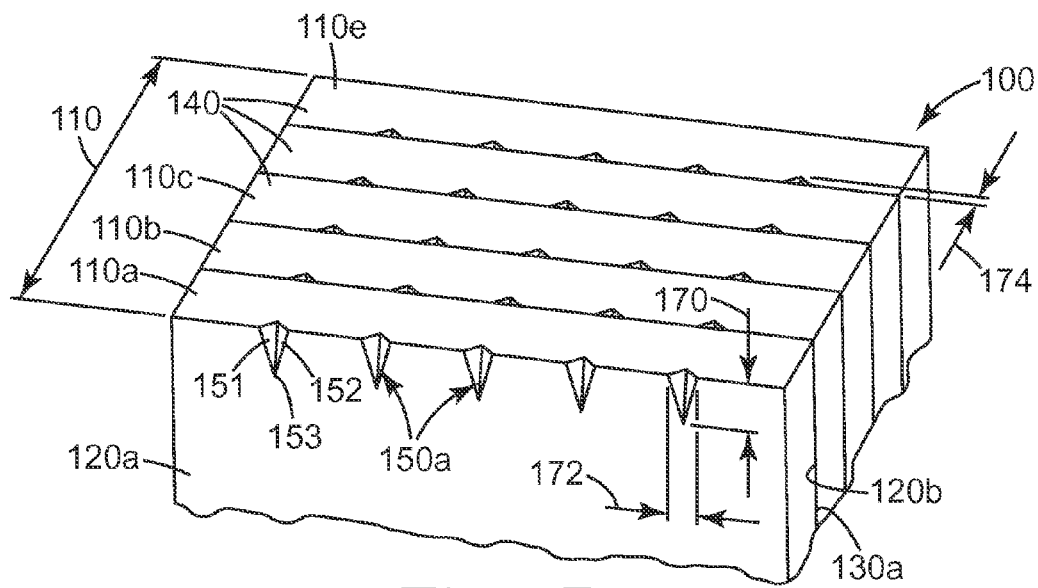
FIG. 1B is an isometric view of stacked laminate mold 100 according to one exemplary embodiment of the present disclosure.

The stacked laminate mold may be further understood by reference to FIG. 1B, which depicts one exemplary embodiment of the stacked laminate mold of the present disclosure. Stacked laminate mold 100 comprises plates 110a, 110b, 110c, ... and 110e (collectively plurality of plates 110) which are contacted together. Each plate comprises a first major surface and a second major surface. Typically, the first major surface and second major surface of each plate are planar, although this is not required so long as they are substantially conforming to one another. As shown in FIG. 1B, plate 110a comprises first major surface 120a and second major surface 130a. Plurality of plates 110 are stacked adjacent to one another such that second major surface 130a of plate 110a is adjacent first major surface 120b of plate 110b. Plurality of plates 110 comprise first mold surface 140, wherein first mold surface 140 connects the first major surface and the second major surface of each plate.

In one embodiment, the first major surface and the second major surface of each plate in the plurality of plates are parallel to one another as shown in FIG. 1B. In another embodiment, the first major surface and the second major surface of a plate in the plurality of plates are not parallel to one another and instead are tapered either in the horizontal direction, the vertical direction, or both directions. The adjacent plate is then tapered in the opposite direction so as to maintain substantial conformation between the second major surface of one plate and the first major surface of the adjacent plate.

As depicted in FIG. 1B, first mold surface 140 of each of the plurality of plates 110 should be carefully formed so as to present a continuous, uninterrupted surface made up of each of the individual mold surfaces.

An exemplary formation of the cavities in the stacked laminate mold is as follows. The plurality of plates 110 comprise a plurality of cavities 150a. Each cavity 150a comprises a V-shaped groove comprising first planar cavity surface 151 and second planar cavity surface 152 meeting at apex 153. As shown in FIG. 1B, cavity 150a is open at least to first mold surface 140. First planar cavity surface 151 and second planar cavity surface 152 intersect each respective plate's first major surface (e.g., 120a) and each respective plate's first mold surface (e.g. 140).

The resulting cavity shape is defined by the intimate contact between the first major surface and second major surface of adjacent plates. For example in FIG. 1C, stacked laminate mold 160 comprises a square pyramidal-shaped cavity defined by cavity 150b on first major surface 121 of plate 111e and cavity 155b on second major surface 131 of plate 111d.

Figure 1C:
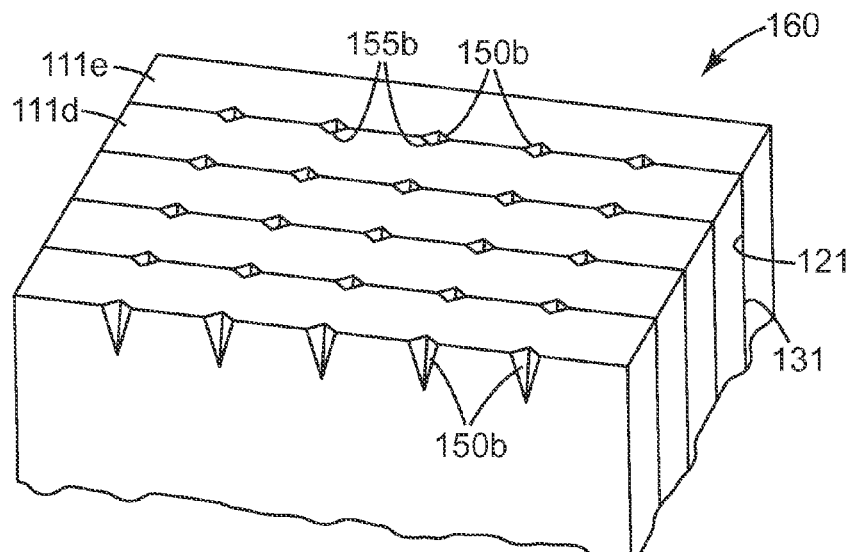
FIG. 1C is an isometric view of stacked laminate mold 160 according to one exemplary embodiment of the present disclosure.

The surface of the cavity can be planar as depicted in FIGS. 1B and 1C or curvilinear. The cavity may have any shape including, for example: a pyramid, a half pyramid, a stepped pyramid, a prism, a cone, a half cone, a stepped cone, a frustum, a standard bevel, short bevel or true short bevel hypodermic shape, a trilobal shape, obelisk, beveled cylinder, or combinations thereof.

The shape and surface of the cavity is not particularly limited, however, the following may be considered when designing the cavity. First, the cavity shape may be limited by the ease of machining the cavity. Second, the cavity may be designed to facilitate the removal of the resulting molded article. For example, an appropriate draft angle greater than at least 0.5 degrees may be designed into the cavity shape to ensure proper removal of the resulting molded article from the mold. This is particularly important when the design involves a cavity having nearly straight walls. Third, the cavity may be designed to provide a resulting molded article that is effective at delivering or extracting fluids and is patient-friendly. For example, the hollow microneedle array must be strong enough to pierce the subject's skin. The strength of the polymeric material used in the hollow microneedle array may dictate the angle of the cavity, e.g., a greater angle would provide greater strength to the hollow microneedle. However, this angular increase may cause greater trauma to the skin of the patient (or subject). Therefore, it may be important to provide a hollow microneedle with a sharp tip and small surface area, which would require minimal force for the hollow microneedle's tip to disrupt the surface of the stratum corneum.

In one embodiment of the present disclosure, the first mold half comprises mold materials of at least one of: steel, steel alloys, aluminum, aluminum alloys, nickel, nickel alloys, copper, copper alloys, beryllium copper, beryllium copper alloys, or combinations thereof.

The cavities may be machined using, for example, milling, cutting, grinding, chemically etching, electrode discharge machining, electrochemical etching, laser ablation, focused ion beam machining, or combinations thereof. Milling tools can be used to cut the cavity including, for example, square end or round end milling machine cutters, a suitable tapered cutting or grinding wheel, or the like. In one embodiment, the cavities are formed by plunger electrode discharge machining using a copper electrode.

The dimensions of the cavity are defined with reference to FIG. 1B as follows. Cavity length 170 is defined as the distance along first major surface 120a from apex 153 to first mold surface 140. Cavity base width 172 is defined as the cavity distance along first mold surface 140 and the respective plate's major surface, e.g., 120a. Cavity base depth 174 is defined as the cavity distance along first mold surface 140, perpendicular to the respective plate's major surface. In some embodiments, such as FIG. 1C, the cavity base depth is the sum of the cavity base depth on adjacent plates.

In one embodiment, the cavities are tapered and have a cavity aspect ratio (cavity length to cavity base width) of at least 0.25 to 1, 1.5 to 1, 3 to 1, 5 to 1, 10 to 1, 15 to 1, 20 to 1, or even 30 to 1. In one embodiment, the cavities have a cavity length of 25 to 3000 μm (micrometers). In some embodiments, the cavity length is at least: 20, 25, 30, 40, 50, 75, 100, 200, 400, 500, 800, 1000, 1500, 2000, or even 2500 μm; at most: 3000, 2800, 2500, 2000, 1500, 1000, 800, 500, or even 250 μm. In one embodiment, the cavities have a cavity base width of 25 to 900 μm. In some embodiments, the cavity base width is at least: 20, 25, 30, 40, 50, 100, 150, 200, 300, 500, or even 700 μm; at most: 900, 800, 700, 600, 500, 250, 100, or even 50 μm. In one embodiment, the cavities have a cavity base depth of 25 to 500 μm. In some embodiments, the cavity base depth is at least: 20, 25, 30, 40, 50, 100, 150, 200, 300, or even 400 μm; at most: 500, 400, 300, 200, 100, or even 50 μm. However, larger and smaller cavities are also within the scope of the present disclosure.

The plurality of cavities on the first mold half is not particularly limited. However, the first mold half typically comprises 1 to 100 cavities. In some embodiments, the plurality of cavities comprises at least 1, 2, 4, 5, 8, 10, 12, 15, 20, 50, or even 75 cavity (cavities); at most 100, 75, 50, 30, 28, 24, 20, 15, 12, 10, 8, or 6 cavities. The cavities may have a center-to-center spacing from 25 to 5000 μm. In some embodiments, the cavities have a center-to-center spacing of at least: 20, 25, 50, 100, 150, 300, 500, 1000, 2000, 3000, or even 4000 μm; at most: 5000, 4000, 3000, 2000, 1000, 750, 500, 250, or even 100 μm. The cavities may be ordered on the surface of the first mold half or they may be random.

The spacing of the cavities may be influenced by the thickness of the plates in the stacked laminate mold, the inclusion of plates without cavities, and the cavity base width within the first mold surface. Thus, the array of cavities may be adjusted between moldings and the area around the perimeter of the array may be adjusted by adding or removing plates in the stacked laminate mold.

FIG. 2 depicts one exemplary embodiment of a second mold half of the present disclosure. Second mold half 200 comprises a second mold surface 210, which is a negative mold for the second major surface (back side) of the resulting molded article. Second mold surface 210 is relatively planar and comprises thereon a plurality of projections 220. As depicted in FIG. 2, second mold half is a single mold, however, in some embodiments, an insert comprising the plurality of projections may be inserted into a frame and held in place.

The projections will be better understood with reference to FIG. 3A. Projection 300 comprises base end 310 (which is in contact with the relatively planar surface of the second mold half), tip end 330, and neck 320 (which connects base end 310 to tip end 330). As shown in FIG. 3A, the base end of the projection may comprise a first drafting angle while the neck of the projection may comprise a second drafting angle. In some instances, the projection may comprise only a first drafting angle, for example, the projection may be a cone. However, the present disclosure has found it advantageous to change the drafting angle of the base end compared to the neck to enable easy release from the resulting molded article.

Shown in FIG. 3A, neck 320 comprises near tip end 330, beveled surface 350 and contact surface 340.

The tip end of the projection may comprise any geometrical shape, such as, for example, a rectangle, square, circle, or a half circle. The tip end of the projection may even be a line comprising a nominal thickness, for example, when two opposing beveled surfaces converge to form a line; or a point, for example, when the surfaces of the neck converge to a single point.

The neck of the projection is designed to: be sufficiently small to be contained within a cavity, enable flow of molten polymeric material into the cavity, allow for easy release from the molded article, and, in some instances, be a conduit or a bore in the resulting molded article. In one embodiment, the neck will comprise at least one beveled surface. The beveled surface enables the flow of molten polymeric material to the apex of the cavity and helps strengthen the tip of the resulting molded article, by allowing a larger cross-sectional area to be filled with polymeric material. In one embodiment, the neck has a length from 25 to 5000 μm. In some embodiments, the neck has a length of at least: 20, 25, 30, 40, 50, 100, 150, 200, 300, 500, 750, 1000, 1500, 2000, 3000, or even 4000 μm; at most: 5000, 4500, 4000, 3000, 2000, 1000, 750, 500, 250, 100, or even 50 μm. The width of the neck is smaller than the width of the cavity to enable the neck of the projection to be inserted into, and at least partially contained within the cavity. In one embodiment, the neck has a maximum neck width of 5 to 800 μm. In some embodiments, the neck width is at least: 5, 7, 10, 15, 20, 25, 30, 40, 50, 100, 150, 200, 300, 500, or even 700 μm; at most: 800, 700, 600, 500, 250, 100, 50, 20, or even 10 μm. The neck may have any shape including, for example, a curved surface (e.g., cylinder) or a planar surface (e.g., rectangular), or combinations thereof. The shape and dimension of the neck will determine the shape and dimension of the bore within the resulting molded article and should be shaped to enable easy release from the resulting molded article. An appropriate draft angle greater than at least 0.5 degrees may designed into the projection to ensure proper removal of the resulting molded article from the mold. This is particularly important when the design involves a neck with nearly straight walls.

The design of the neck and tip portion is not particularly limited and is preferably designed in combination with the cavity shape to create different hollow microneedle arrays. For example, shown in FIG. 3B is another embodiment of a projection, which comprises a cross-head shape, similar to a Phillips screw-driver. Projection 305 comprises base end 315 and neck 325. Neck 325 comprises four contact surfaces (345a and 345b shown) and beveled surfaces (355a, 355b, and 355c shown).

The base end of the projection connects the neck to the relatively planar surface of the second mold. The base end provides structural support to the neck and tip end of the projection. For example, a larger base end provides more structural stability to the more fragile neck during alignment and filling of the mold assembly. The maximum base end area is at least 2, 3, 4, 5, 8, 10, 15, 20 or even 50 times larger than the tip end of the projection. Typically, the base end may be formed in any suitable shape, such as, for example, a cone (e.g., elliptical, circular, or polygonal base), frustum (i.e., truncated cone), cube, truncated cube, or polyhedron. For example, base end 310 in FIG. 3A is truncated-conical in shape, larger in diameter where connected to the relatively planar surface of the second mold half and smaller in diameter where connected to the neck. In one embodiment, the base end has a projection base height (distance from the neck of the projection to the relatively planar surface of the second mold half, perpendicular to the second mold half) of 25 to 2000 μm. In some embodiments, the projection base height is at least: 20, 25, 30, 40, 50, 100, 150, 200, 300, 500, or even 1000 μm; at most: 2000, 1500, 1000, 900, 800, 700, 600, 500, 250, 100, or even 50 μm. In one embodiment, the base end has a projection base width (distance across the widest portion of the projection base parallel to the relatively planar surface of the second mold half) of 25 to 3000 μm. In some embodiments, the projection base width is at least: 20, 25, 30, 40, 50, 100, 150, 200, 300, 500, 1000, 1500, 2000, or even 2500 μm; at most: 3000, 2500, 2000, 1500, 1000, 900, 800, 700, 600, 500, 250, 100, or even 50 μm.

In one embodiment of the present disclosure, the second mold half comprises mold materials of at least one of: steel, steel alloys, aluminum, aluminum alloys, nickel, nickel alloys, copper, copper alloys, beryllium copper, beryllium copper alloys, or combinations thereof.

The projections may be machined using, for example, milling, cutting, grinding, chemically etching, electrode discharge machining, electrochemical etching, laser ablation, focused ion beam machining, or combinations thereof. Milling tools can be used to cut the projections including, for example, square end or round end milling machine cutters, a suitable tapered cutting or grinding wheel, or the like.

The number and arrangement of the plurality of projections on the second mold half is not particularly limited. However, the second mold half typically comprises 1 to 100 projections. In some embodiments, the plurality of projections comprises at least 1, 2, 4, 5, 8, 10, 12, 15, 20, 50, or even 75 projection(s); at most 100, 75, 50, 30, 28, 24, 20, 15, 12, 10, 8, or 6 projections. The plurality of projections may have a center-to-center spacing from 25 to 5000 μm. In some embodiments, the projections have a center-to-center spacing of at least: 20, 25, 50, 100, 150, 300, 500, 1000, 2000, 3000, or even 4000 μm; at most: 5000, 4000, 3000, 2000, 1000, 750, 500, 250, or even 100 μm. The projections may be ordered on the surface of the second mold half or they may be random.

Generally, the order of the projections of the second mold half are identical in position and spacing as the cavities in the first mold half so as to align each projection with each cavity. Although also contemplated are methods in which the number of cavities on the first mold is not the same as the number of cavities on the second mold half. For example, in one embodiment, the second mold half contains fewer projections than the first mold half contains cavities, resulting for instance in an article having both solid and hollow microneedles.

According to the present disclosure, hollow microneedle arrays are achieved by contacting the first mold half with the second mold half to create a mold assembly, melting the polymeric material to fill the mold assembly, solidifying the polymeric material, and then detaching the solidified polymeric material from the mold assembly.

Figure 4A:
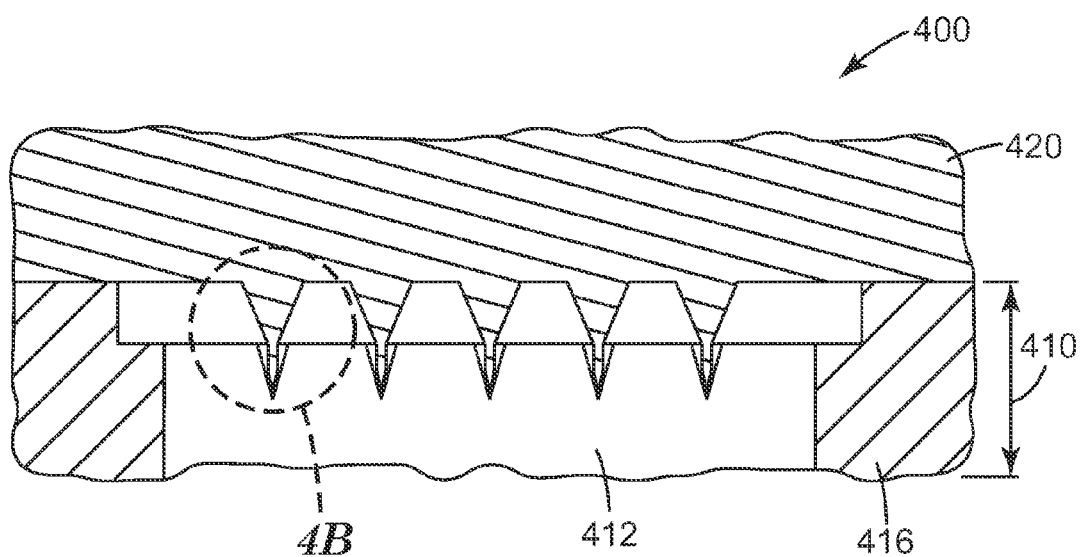
FIG. 4A is schematic side-view of mold assembly 400 according to one exemplary embodiment of the present disclosure.

In one embodiment, the first mold half and the second mold half are contacted as shown in FIG. 4A to form mold assembly 400. Mold assembly 400 comprises first mold half 410 including stacked laminate insert 412 and frame 416, and second mold half 420. As shown in FIG. 4A, the plurality of projections on the first mold half are aligned with the plurality of cavities of the second mold half.

The first mold half and second mold half are contacted together via physical means, using for example, side and/or parting taper locks for alignment of the mold halves. Active alignment, involving mechanical means, is used to register (i.e., each projection is aligned within their respective cavity) the mold halves. In one embodiment, the registering is less than 10, 7, 5, 4, 2, or even 1 μm.

Although the projections may be contained within each cavity, there may be slight misalignment due to fabrication tolerances, inconsistent thermal expansion of the projections, and alignment of the mold halves. Thus, the interaction between each projection/cavity pair may not be identical. An advantage of the present disclosure is the ability of the projections to self-align, enabling each projection to be located in a substantially similar position within each cavity. For example, a cavity having a cavity base width of 300 μm may be misaligned relative to the projection by 30 μm (10% center to center misalignment), which may be mitigated with the self-alignment feature of the projections.

The slight misalignment may be overcome by the design of the cavities and the projections. For example, the pyramid-shaped cavities may guide the projections, and the projections, based on their composition, may have the ability to flex somewhat independently of the other projections as the mold closes.

In one embodiment, passive alignment may be used to more precisely align the projections within each cavity. Passive alignment involves using independent thermal control of each of the mold halves to enable even tighter registration of the mold halves once the cavities and projections are under load. If improper alignment of the mold halves is achieved, this could potentially damage the fine features of the mold or potentially cause catastrophic failure of the mold. Passive alignment using independent temperature control of the mold base, the mold frame that houses the stacked laminate mold insert, and the stacked laminate molds themselves, ensures that proper control is achieved over the coefficient of thermal expansion of each of the mold materials that make up each of the mold halves. For example, over-expansion of the projections (inadequate passive alignment) relative to the mold cavities, could lead to damage to the cavity surfaces or the projection features themselves. Appropriate expansion of the projections using passive alignment may lead to a near perfect contact between the desired contact surface of the projection and the cavity surface.

This passive alignment may be achieved using dynamic temperature control. Dynamic temperature control may be performed by heating or cooling of the mold halves using, for example, at least one of: inductivity, electricity, lasers, infrared radiation, resistivity, ultrasound, water, steam, oil, or combinations thereof.

To facilitate the dynamic temperature control, typically the mold halves comprise different mold materials. In one embodiment, the cavity surface and the plurality of projections comprise different mold materials. For example, the cavity surface may comprise at least one of: hardened H13, P20, spring steel, 420 stainless steel, or combinations thereof; and the projections may comprise of at least one of: S7 steel, A2 steel, D2 steel, nickel, or combinations thereof.

Figure 4B:
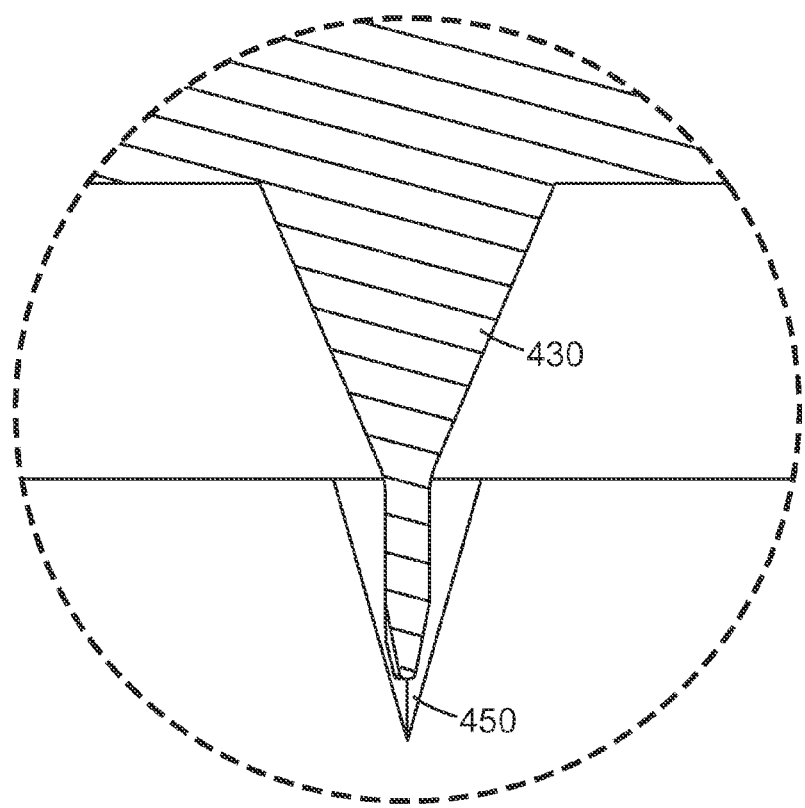
FIG. 4B is an enlarged view of clamped mold assembly 400 according to one exemplary embodiment of the present disclosure.

Shown in FIG. 4B is an enlarged schematic of mold assembly 400 depicting projection 430 inside of cavity 450. In some embodiments, the projection is in contact (e.g., intimate contact) with the surface of cavity. In some embodiments, the projection is not in contact with the cavity surface.

By selecting different mold materials for the projections and the cavity surfaces, the projections can be manufactured to flex within the cavity so as to not damage the cavity surface or itself during mold alignment. The non-damaging nature of the projection/cavity alignment and the material selection, enables the mold halves to be used repeatedly, which leads to high volume use.

The choice of the specific modulus, which defines the stiffness to weight ratio of the mold material, allows either the cavity surfaces or projections to have minimal structural weight based on their design, which can withstand significant deflection or deformation as a result of an applied load. During molding of the hollow microneedle array, specific modulus of the cavity and projections is an important consideration. Self-alignment of the projections against the cavity surface is possible by utilizing projections with a lower specific modulus relative to the cavity surface in order to allow the projections to "flex" under the applied load during clamping. Selecting the appropriate specific modulus will increase the lifetime of both the projections and cavities. In one embodiment, the cavity surface comprises a first mold material and the projection comprises a second mold material, wherein the first mold material has a specific modulus that is at least 30, 20, 15, or even 10 GPa (giga Pascal) higher than the specific modulus of the second mold material.

Specific strength is related to the strength and density of a material. Specific strength defines the breaking length or self-supporting length of the material. Selecting a mold material of the projection with a higher specific strength than the cavity surface material ensures a higher lifetime of both the projections and cavities. In one embodiment, the cavity surface comprises a first mold material and the projection comprises a second mold material, wherein the first mold material has a specific strength that is at least 0.2, 0.5, 1, or even 2 GPa higher than the specific strength of the second mold material.

Hardness is defined as the resistance to a change in shape of the mold material as a result of an applied force or load. Because of the expense associated with fabricating mold masters, generally it is desirable to maintain the integrity of the mold and not allow it to get scratched, corroded, etc. to ensure a higher lifetime of both the projections and the cavities. In one embodiment of the present disclosure, the cavity surface comprises a first mold material and the projection comprises a second mold material, wherein the second mold material has a hardness that is greater than the hardness of the first mold material. In another embodiment of the present disclosure, the cavity surface comprises a first mold material and the projection comprises a second mold material, wherein the first mold material has a hardness that is greater than the hardness of the second mold material. For example, the cavity surface comprises a first mold material and the projection comprises a second mold material, wherein the first mold material has a hardness that is at least 20, 25, 30, 35, or even 50 Rockwell C higher than the hardness of the second mold material.

Figure 5A:
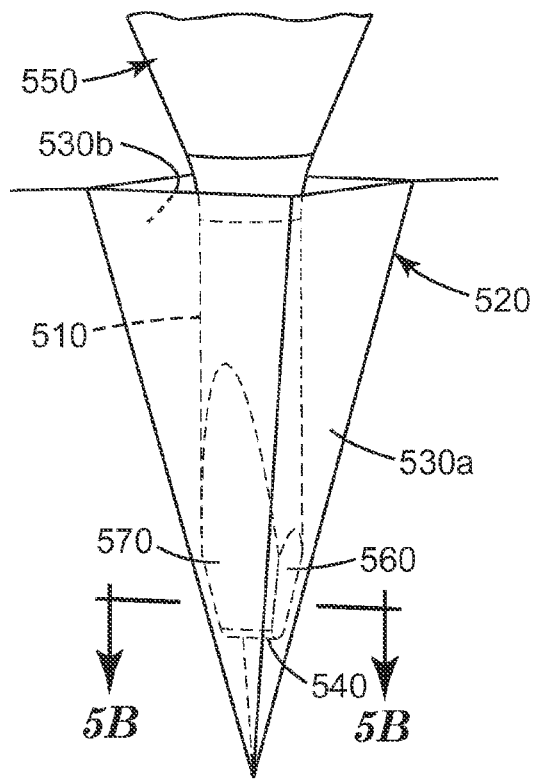
FIG. 5A is an isometric view of projection 550 positioned inside of cavity 520 according to one exemplary embodiment of the present disclosure.

The interaction of the projection with the cavity will be better understood with reference FIG. 5A. In FIG. 5A, projection 550 is inserted into cavity 520, which is a square pyramid. As shown in FIG. 5A, tip end 540 and at least a portion of neck 510 are contained within cavity 520. Cavity 520 comprises cavity surfaces 530b (front) and 530a (right side). Contact surface 560 of projection 550 is in intimate contact with cavity surface 530a. Beveled surface 570 of projection 550 is not in contact with cavity surface 530b.

Figure 5B:
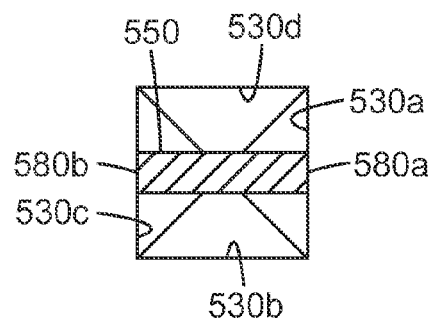
FIG. 5B is a section off of section lines 5B in FIG. 5A, according to one exemplary embodiment of the present disclosure.

FIG. 5B is a planar cross-section of FIG. 5A taken off of section lines 5B in FIG. 5A. As shown in FIG. 5B, projection 550 contacts cavity surfaces 530a and 530c at areas 580a and 580b. Projection 550 does not contact cavity surfaces 530b or 530d.

Contact surface 560 is in intimate contact with cavity surface 530a, while the beveled surface 570 is not in contact with cavity surface 530b. As molten polymeric material fills cavity 520, the molten material will flow around projection 550 and will be able to access the apex of cavity 520 via the space left by beveled surface 570. Because contact surface 560 is in intimate contact with cavity surface 530a, the molten polymeric material is prevented from contacting the cavity surface at areas 580a and 580b and thus two opposed orifices will be present in the resulting molded article.

Figure 5C:
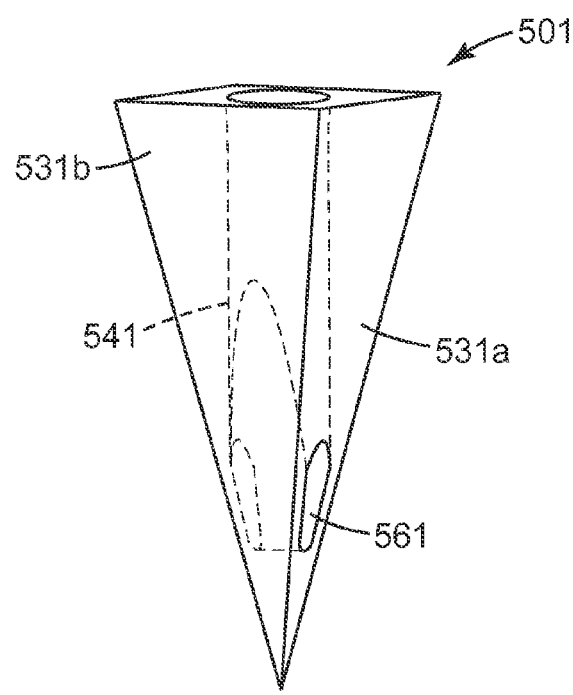
FIG. 5C is an isometric view of hollow microneedle 501 resulting from the cavity and projection of FIGS. 5A and 5B.

After the molten polymeric material is cooled and hardened, the mold halves are separated and the resulting molded article (e.g., the hollow microneedle array) is removed. The resulting molded article 501 is shown in FIG. 5C, which depicts a square pyramidal-shaped structure with orifice 561 on article surface 531a and no orifices on article surface 531b. Also shown in FIG. 5C is bore 541 (resulting from the neck 510), which is in fluid communication with orifice 561 (resulting from contact surface 560).

In FIG. 5A, the cavity and projection are symmetric, therefore, although not shown in FIG. 5C, article 501 comprises two orifices 561, one on right side of article surface 531a (right side of square pyramid), and one on the opposed side (left side of square pyramid, not shown), whereas the front side article surface 531b and the opposed back side of article 501 do not include an orifice.

FIG. 8A is another embodiment depicting the interaction of a projection with a cavity. In FIG. 8A, projection 850 is inserted into cavity 820, which is a square pyramid. As shown in FIG. 8A, tip end 880 and at least a portion of neck 810 are contained within cavity 820. Cavity 820 comprises cavity surfaces 830a (right back), 830b (right front), 830c (left front) and 830d (left back). Contact surfaces 890a, 890b, and 890c of projection 850 are in intimate contact with cavity surfaces 830b, 830c, and 830d, respectively. Beveled surface 870 of projection 850 is not in contact with cavity surface 830a.

FIG. 8B is a planar cross-section of FIG. 8A taken at tip end 880. As shown in FIG. 8B, tip end 880 contacts cavity surfaces 830b, 830c, and 830d at contact surfaces 890a, 890b, 880c, and 880d. Projection 850 does not contact cavity surface 830a.

Contact surfaces 890a, 890b, and 8901c are in intimate contact with cavity surfaces 830b, 830c, and 830d, respectively, while the beveled surface 870 is not in contact with cavity surface 830a. As molten polymeric material fills cavity 820, the molten material will flow around projection 850 and will be able to access the apex of cavity 820 via the space left between tip end 880 and the cavity surfaces, a majority of the molten polymeric material may reach the apex of cavity 820 by the space left by beveled edge 870.

After the molten polymeric material is cooled and hardened, the mold halves are separated and the resulting molded article is removed. The resulting molded article 801 is shown in FIG. 8C, which depicts a square pyramidal-shaped structure with orifices 861 on article surfaces 831b, 831c and 831d and no orifices on article surface 831a. Also shown in FIG. 8C is bore 841 (resulting from neck 810), which is in fluid communication with orifice 861 (resulting from contact surface 890b).

FIG. 9A is yet another embodiment depicting the interaction of a projection with a cavity. In FIG. 9A tip end 980 of projection 950 intimately contacts cavity surfaces 990a, 990b, 990c, and 990d of cavity 920 with contact surfaces 990a, 990b, 990c, and 990d. FIG. 9B is a planar cross-section of FIG. 9A taken at tip end 980 showing tip end 980 comprising a majority of the cavity area. The resulting molded article 901 is shown in FIG. 9C, which depicts a square pyramidal-shaped structure with orifices 961 on resulting molded article surfaces 931a and 931b (shown) and bore 941, which is in fluid communication with orifices 961.

Designs, other than those disclosed above, for the cavity and projection are contemplated including various geometries of the cavities and projections, and multiple areas of contact, such as, for example, 5, 6, 8, or even 10, so long as the resulting molded article is structurally sound and durable and there is enough space between the tip end of the projection and the cavity surface to enable molten polymeric material to reach the cavity's apex.

Figure 6:
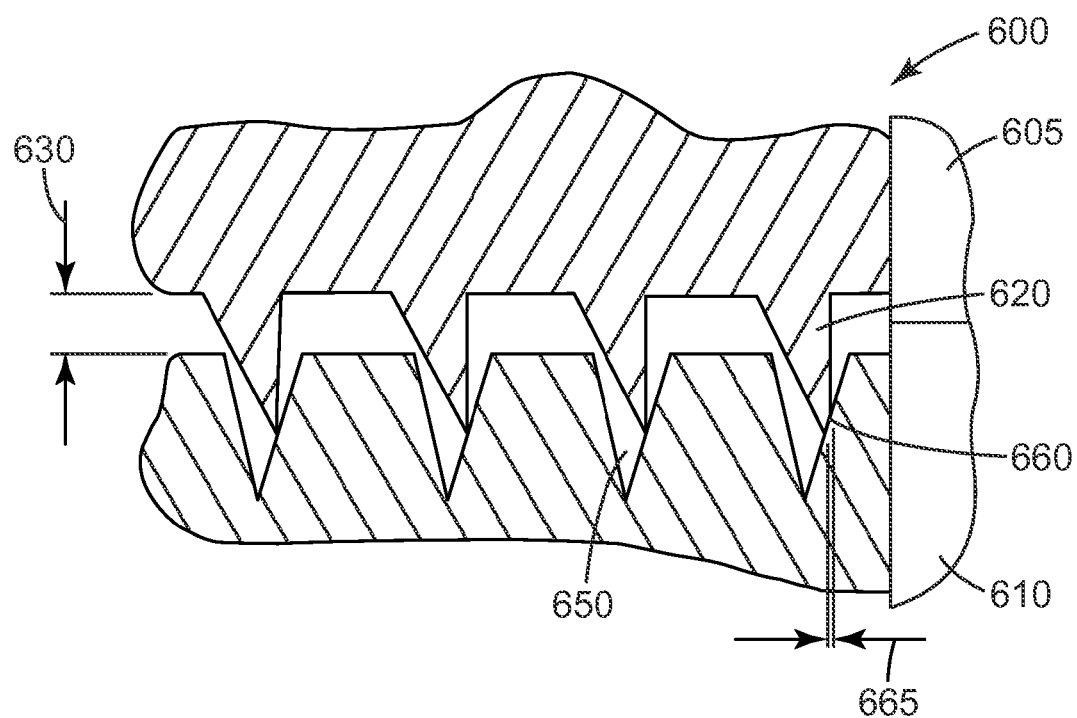
FIG. 6 is a schematic side-view of mold 600 according to one exemplary embodiment of the present disclosure.
Figure 7:
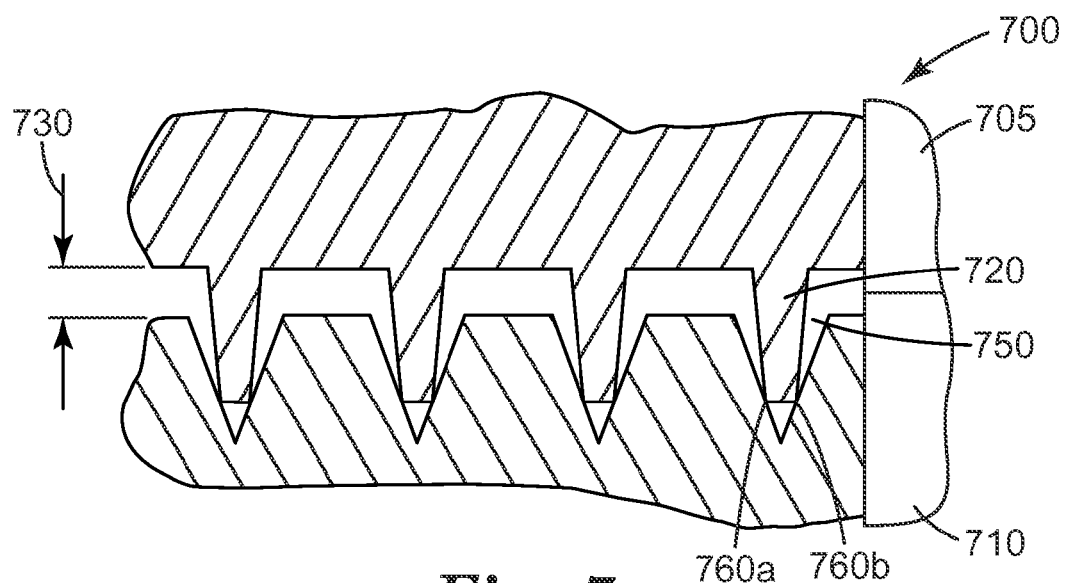
FIG. 7 is a schematic side-view of mold 700 according to one exemplary embodiment of the present disclosure.

The filling of the molten polymeric material in the mold assembly is further depicted in FIGS. 6 and 7. In one embodiment, FIG. 6 depicts a side view of mold assembly 600 comprising first mold half 610 in contact with second mold half 605. As shown in FIG. 6, the distance between at least a portion of the neck of the projection and the cavity surface is variable with projection 620 in contact with the cavity surface at 660. The area of contact 665 may determine the size and shape of the orifice in the resulting molded article. Molten polymeric material fills the area between the planar surfaces of the first mold surface and the second mold surface. Because of the space between the neck of the projection and the cavity surface, molten polymeric material will fill in around projection 620 into the apex of cavity 650. In this embodiment, at least one cavity surface is not in contact with the projection. The length 630 between the planar surfaces of the first mold surface and the second mold surface may define the thickness of the support base of the resulting molded article.

In another embodiment, FIG. 7 depicts a side view of mold assembly 600 comprising first mold half 710 in contact with second mold half 705. Projection 720 is in contact with cavity surface at 760a and 760b. Molten polymeric material fills the area between the planar surfaces of the first mold surface and the second mold surface. Because of the space between the neck of the projection and the cavity surface, molten polymeric material will fill in around projection 720 into the apex of cavity 750. In this embodiment at least two cavity surfaces are in contact with the projection with the resulting molded article comprising at least two orifices. The length 730 between the planar surfaces of the first mold surface and the second mold surface may define the thickness of the support base of the resulting molded article.

It is possible to use the mold halves described herein to mold an article having different regions or groups. Each region or group may contain a group of like cavities or projections, with the cavities or projections differing from region to region. Such differences can be in cavity or projection size, configuration, orientation, or combinations thereof.

Various molding techniques, as are known in the art, including for example: compression molding, thermal embossing, thermoplastic (TP) or thermoset (TS) injection molding (IM), injection-compression molding (ICM), powder injection molding (PIM), liquid injection molding (LIM), reactive injection molding (RIM), ceramic injection molding (CIM), metal injection molding (MIM) and cast extrusion; may be envisioned using the mold halves as described herein.

In one embodiment, the plurality of projections is inserted into the plurality of cavities before contacting at least the first mold surface or the second mold surface with polymeric material. TPIM, TSIM, ICM, PIM, LIM RIM, CIM, or MIM may be used to replicate the hollow microneedle array based on the processes known in the art for each of these techniques. Traditional injection molding techniques will involve injection of molten polymeric material between the void space covered by the plurality of projections contacting the plurality of cavities. The molten polymeric material is injected at relatively high pressure and left to cure, set or cool prior to removal of the resulting molded article from the mold assembly.

In another embodiment, at least the first mold surface or the second mold surface is contacted with polymeric material before inserting the plurality of projections into the plurality of cavities. Processes such as thermal embossing or compression molding may be used to apply uniform pressure between the plurality of projections contacting the plurality of cavities. This uniform pressure is applied over a specific period of time concurrently with the softening of the polymeric material in the mold assembly.

In one embodiment, the injection of the molten polymeric material may be performed in conjunction with velocity and/or packing or injection pressure control used to aid in allowing the molten polymeric material to fill the first mold half. In one embodiment, this pressure may be greater than about 6,000 psi, 10,000 psi, or even 20,000 psi (pounds per square inch).

In one embodiment, it may be desirable to add a compressive force or coining to the molten polymeric material in the first mold half in order to assist in filling the cavities, such as described in U.S. Pat. Publ. 2008/0088066 A1 (Ferguson et al.). Additional details regarding injection-compression molding may be found in U.S. Pat. No. 4,489,033 (Uda et al.), U.S. Pat. No. 4,515,543 (Hamner), and U.S. Pat. No. 6,248,281 (Abe et al.).

Typically when molding articles, venting of the cavity is required. Venting serves as an exit region near the mold cavity to allow displaced air to leave the cavity, thus allowing for more uniform filling of the mold cavity with molten polymeric material. Typically, venting of mold halves is provided by primary and secondary vents, which are typically 10 and 100 µm deep channels, respectively. The primary and the secondary vents are cut into the major surface of the first mold half of the mold to direct air away from the cavity. The primary vent ensures a path for air to escape while also prohibiting the molten polymeric material from entering because of the large viscosity difference compared to air. The secondary vent ensures that the air being evacuated can freely flow out through the parting line of the mold half. Venting may also be achieved through the ejection pins used to remove the resulting molded article from the mold. While these primary and secondary vents help ensure rough evacuation of the air for the macroscopic portion of the cavity, they do not help mitigate short filling of the respective cavities, resulting in incomplete fill of the cavity and the resulting molded article having a tip diameter far larger than the cavity.

In one embodiment of the present disclosure, venting of the plurality of cavities is provided by submicrometer spacing between the plurality of plates. In the first mold half, each respective plate's first major surface and second major surface are not polished, leaving a slight roughness to each major surface. Although the plurality of plates are in intimate contact with one another, the submicrometer roughness of plates enables the air forced to leave the cavity to be vented in between adjacent plates. Further, because the venting is in the submicrometer range, the molten polymeric material is contained within the cavity due to its much higher viscosity relative to the evacuated air. The submicrometer venting allows for full air evacuation within the stacked laminate mold, which in turn allows for thermoplastic injection molding at mold temperatures 10 to 20° F. cooler, reduced injection pressures 25 to 30%, shorter cycle times (20 to 30 sec faster), and increases in both the mold and micro-tooling life. The submicrometer venting also enables sharper tip sizes in the resulting molded article. For example, in one embodiment, a hollow microneedle according to the present disclosure has a tip diameter of 20, 10, 7, 5, 2, 1, 0.8, or even 0.5 µm or less.

The plurality of plates comprise a surface roughness over substantially the entire area of each plate's first and second major surface is less than 30 RMS (root mean square) pinch (0.762 RMS µm), 20 RMS pinch (0.508 RMS µm), 10 RMS pinch (0.254 RMS µm) or even 4 RMS pinch (0.102 RMS µm).

In one embodiment, venting of the plurality of cavities may comprise a primary and/or secondary vent as is traditionally used in the art.

The resulting molded article (e.g., hollow microneedle array) may be manufactured from a variety of materials. Material selection may be based on a variety of factors including the ability of the material to accurately reproduce the desired pattern; the strength and toughness of the material when formed into the hollow microneedle array; the compatibility of the material with, for example, human or animal skin; the compatibility of the materials with any fluids that will be expected to contact the hollow microneedle array, etc.

Suitable polymeric materials for the hollow microneedle array of the present disclosure may include, for example: polycarbonate, cyclic olefin copolymer, liquid crystal polymer, polyacrylate, acrylate copolymer, polystyrene, polypropylene, polyethylene, polyester, polyamide, polyamide imide, polyetheretherketone, polyetherimide, polybutylene terephthalate, polyphenyl sulfides, acetals, polyethylene terephthalates polyvinyl chloride, polymethylmethacrylate, acrylonitrile-butadiene styrene, or combinations thereof.

It may be preferred that the polymeric materials have one or more of the following properties: high tensile elongation at break, high impact strength, and high melt-flow index. In one aspect, the melt-flow index as measured by ASTM D1238 (conditions: 300° C., 1.2 kg weight) is greater than about 5 g/10 minutes. The melt-flow index as measured by ASTM D1238 (conditions: 300° C., 1.2 kg weight) is greater than about 10 g/10 minutes, or even between about 20 g/10 minutes and 30 g/10 minutes. In one aspect, the tensile elongation at break as measured by ASTM D638 (2.0 in/minute) is greater than about 100%. In one aspect, the impact strength as measured by ASTM D256, "Notched Izod", (73° F., 23° C.) is greater than about 5 ft-lb/inches (265 J/m).

Depending on the molding technique used, either the mold assembly is heated to melt a sheet of polymeric material or molten material is injected into the mold assembly. The heating of the first and/or second mold halves above the softening temperature of the polymeric material allows the polymeric material to substantially fill the cavities and micrometer features in the mold assembly. It is important that the polymeric material not be allowed to substantially cool before filling the micrometer features, since it can "skin over" or solidify in the cavities prior to complete filling and block further flow of molten material.

The "softening temperature" refers to the temperature at which a polymeric material will soften and deform when subject to ordinary forces, such as those encountered during detachment of a resulting molded article from a mold half. This may be conveniently measured by the Vicat softening temperature, which measures the temperature at which a flat-ended needle penetrates into a test sample (under conditions, for example, of a 50 N loading on the needle and a rate of temperature increase of 120° C./h as described in ASTM D1525-00). For amorphous materials, the softening temperature will be governed by the glass transition of the material, and in some instances the glass transition temperature will be essentially equivalent to the Vicat softening temperature. The glass transition temperature may be measured by methods known to one skilled in the art, such as by differential scanning calorimetry using a typical scanning rate of 10° C./min.

After molten polymeric material fills the cavities, the mold assembly is then cooled to a temperature at least below the softening temperature of the polymeric material. Finally, the resulting molded article is detached from the mold assembly. The resulting molded article may be removed from the mold assembly using techniques known in the art, including for example: ejection pins, lifters, stripper sleeves, or air assistance.

One manner in which the resulting molded article (e.g., hollow microneedle) of the present disclosure may be characterized is by height. The height of the hollow microneedle may be measured from the relatively planar resulting molded article support base. In one embodiment, the height of the hollow microneedle is 3000 µm or less, 2500 µm or less, 2000

µm or less, 1500 µm or less, 1000 µm or less, 750 µm or less, 500 µm or less, 300 µm or less, or even 100 µm or less, as measured from the base of the hollow microneedle to the apex. In one embodiment, the height of the hollow microneedle is greater than 90%, or even greater than about 95% of the corresponding cavity length in the first mold half. The hollow microneedles may deform slightly or elongate upon ejection from the mold assembly. This condition is most pronounced if the molded material has not cooled below its softening temperature, but may still occur even after the material is cooled below its softening temperature. In one embodiment, that the height of the hollow microneedles is less than about 115% or even less than about 105% of the cavity length in the first mold half. In one embodiment, the height of the hollow microneedle is substantially the same (e.g., 95% to 105%) as the corresponding cavity length in the first mold half.

The general shape of the hollow microneedles of the present disclosure is tapered. For example, the hollow microneedles have a larger base at the resulting molded article support base and extend away from the resulting molded article support base, tapering to an apex. In one embodiment the shape of the hollow microneedle is pyramidal. In another embodiment, the shape of the hollow microneedle is generally conical.

Figure 10A:
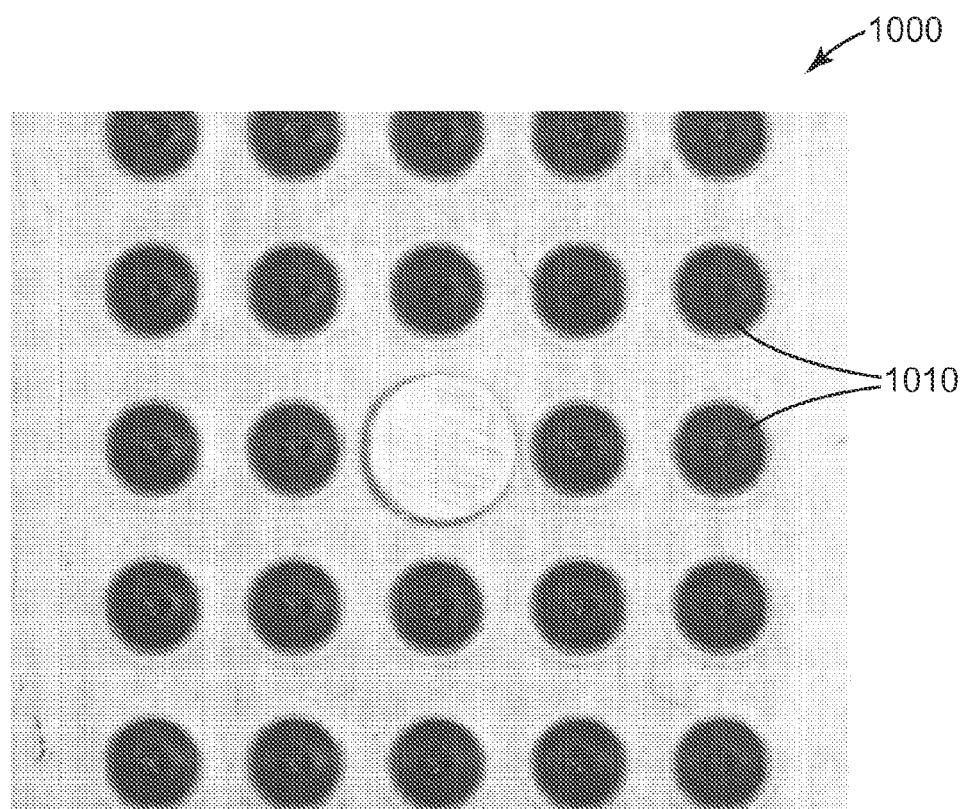
FIG. 10A is a top-view picture of hollow microneedle array 1000 according to Example 6.

The hollow microneedles may be arranged in any desired pattern or distributed over the resulting molded article surface randomly. As shown in FIG. 10A, the hollow microneedles are arranged in uniformly spaced rows placed in a rectangular arrangement. In one embodiment, hollow microneedle arrays of the present disclosure have a patient-facing surface area of more than about 0.1 cm$^2$ and less than about 20 cm$^2$, or even more than about 0.5 cm$^2$ and less than about 5 cm$^2$. In one embodiment, a portion of the resulting molded article surface is non-patterned. In one embodiment the non-patterned surface has an area of more than about 1% and less than about 75% of the total area of the device surface that faces a skin surface of a patient. In one embodiment the non-patterned resulting molded article surface has an area of more than about 0.10 in.$^2$ (0.65 cm$^2$) to less than about 1 in.$^2$ (6.5 cm$^2$). In another embodiment (not shown), the hollow microneedles are disposed over substantially the entire surface area of the resulting molded article.

Another manner in which the hollow microneedles of the present disclosure may be characterized is based on the aspect ratio of the hollow microneedles. The hollow microneedle aspect ratio is the ratio of the microneedle height (distance from the base of the microneedle to the apex) to the maximum base dimension, that is, the longest straight-line distance that the microneedle base occupies on the support base of the resulting molded article.

Generally the microneedles are attached to a support base to provide support. The thickness of the support base can be of any size; however, the important criterion is that the support base be thick enough to be mechanically sound so as to retain the microneedle structure as it is used to penetrate the skin.

Another manner in which the hollow microneedles of the present disclosure may be characterized in the presence of an orifice (or opening) in the hollow microneedle. In one embodiment, the hollow microneedle comprises an orifice that is in fluid communication with the bore. This may be achieved by the contacting of the tip end of the projection with the cavity surface enabling a portion of the cavity surface to not comprise the polymeric material. In this method, generally the size of the orifice in the resulting molded article is influenced by the contact area between the contact surface of the projection and the cavity surface. In another embodiment, the hollow microneedle may be laser drilled to enable an orifice to be in fluid communication with the bore or to enlarge, reshape, or smooth the edges of the orifice. In this method, generally the size of the orifice in the resulting molded article is influenced by the wavelength, power, and exposure time of the laser.

The design of the orifice is not particularly limited and will generally be designed to enable sufficient delivery of fluids to or extraction of fluids from a subject. The orifice may have any shape including, for example, a circle, half circle, an ellipse, a trapezoid, or any regular or irregular polygon shape. The orifice should be large enough to allow fluids to be injected or extracted from a subject. In one embodiment, the area of the orifice is 20,000, 15,000, 10,000, 8,000, 6,000, 5,000, 4,000, 3,000, 2,000, 1000, 750, 500, 300, 100, 75, 50, 30, 25, 10, 5, or even 2 µm$^2$ or less as measured by the cross-section area on the resulting molded article's surface.

The distance between the apex of the hollow microneedle to the center of the orifice on the hollow microneedle will influence the extent to which fluid can be delivered or extracted from the subject. In one embodiment, this distance is 500, 400, 300, 200, 100, or even 50 µm or less. Typically this distance is between 200 to 400 µm depending on the height of the hollow microneedle and the hollow microneedle aspect ratio. If the distance between the apex of the hollow microneedle to the center of the orifice is too large, it could prevent proper delivery or extraction of fluid from the subject.

The presence of an orifice in fluid communication with the bore, enables the hollow microneedles of the present disclosure to be used to inject fluid into a body or extract fluids from a body. The surface that bares the bore in fluid communication with the orifice, can be hermetically sealed with a foil, pouch or ultrasonically welded to another molded component or reservoir that is empty or that holds liquid or fluid for transdermal delivery.

The hollow microneedle array may then be placed in fluid communication with another structure, such as a means for measuring certain characteristics of sampled fluid or a reservoir for holding a drug or biological material for delivery across a biological barrier (e.g., skin). In the fluid delivery embodiments of the present disclosure, the bore and orifice of the hollow microneedle acts to transfer drugs, formulation or biological materials from a reservoir containing the fluid or material to be delivered. In the fluid extraction embodiments of the present disclosure, the bore and orifice of the hollow microneedle acts to sample fluids, such as interstitial fluid or whole blood, for collection and/or testing for various analytes.

The resulting molded articles of the present disclosure may be net-shaped (i.e., a finished product is achieved in a single step process). Therefore no secondary operation such as milling or grinding of the resulting molded article is necessary, which may lead to unwanted residue and contamination of the resulting molded article. Further, because of the machining process used to make the molds and the self-alignment of the molds, high fidelity (i.e., identical replication) of the hollow microneedles across the array may also be achieved.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

EXAMPLES

The following specific, but non-limiting examples will serve to illustrate the disclosure.

First Mold Half
  Cavity Mold 1:
  A first mold half comprising a stacked laminate mold with a plurality of cavities was fabricated by IBM Corp., Rochester, Minn. as follows. The stacked laminate mold comprised twenty stainless steel plates made of 420 stainless steel shimstock, wherein the surface roughness of each major surface of each plate was approximately 0.30 RMS µm. The dimensions of each plate were: 16 mm in length, 10.2 mm in width, and 0.50 mm in thickness. Two holes were drilled through the major surfaces of each plate to allow the plates to be pinned together using 1.6 mm dowel pins. The plates were pinned together and then the mold surface and all four edges of the stacked laminate were ground to provide continuous, coplanar surfaces. The plates were numbered for reference and separated.

Five cavities having the shape of a half pyramid as cut across the diagonal (see, for example, cavity 150a in FIG. 1A) were machined into one major surface of ten plates using Electrode Discharge Machining (EDM), leaving ten plates not machined (or blank). The plates were then wedge-blocked into a laminate holder insert as follows: 3 blank plates; 5 sets of 2 machined plates aligned to form a square pyramidal-shaped cavity followed by one blank plate; and 2 blank plates. The reference numbers were used to ensure that the plates were in the same order as when pinned for grinding. The cavities in the plates were machined such that when the plates were stacked together they formed an array of square pyramidal-shaped cavities. No primary or secondary vents were machined into the plates. In Cavity Mold 1, one of the center cavities in the array was not fabricated into the mold to allow for alignment with an ejector pin on the second mold half, so Cavity Mold 1 comprised a total of 24 square pyramidal-shaped cavities.

The overall first mold half was square having a 1.216 cm side wall dimension. Individual cavities on the first mold half were square pyramidal-shaped (four side walls) with a cavity length of 508 µm and a cavity base width of 300 µm, thus, giving a cavity aspect ratio of 1.67:1. The cavities were spaced in a regular array with a distance of 1513 µm between the apexes of the adjacent cavities. The apex of the cavity had a diameter of 5 µm or less.

Cavity Mold 2:
  A first mold half comprising a stacked laminate mold with a plurality of cavities was fabricated by Detail Tool and Engineering, Blaine, Minn. The machining as described in Cavity Mold 1 above was repeated with the following exceptions. Six plates were used instead of 20 and each major surface had a surface roughness of 0.36 RMS µm. The dimensions of each plate were: 18 mm in length, 10.7 mm in width, and 1.8 mm in thickness. Five cavities were cut into both the major surfaces of four plates and into one major surface of two plates. The six plates were wedge-blocked into a laminate holder and aligned to form a 5×5 array of square pyramidal-shaped cavities. No primary or secondary vents were machined into the plates. Cavity Mold 1 comprised a total of 25 square pyramidal-shaped cavities.

Individual cavities on the first mold half were square pyramidal-shaped with a cavity length of 900 µm and a cavity base edge length (distance along one side of the cavity edge) of 360.7 µm.

Second Mold Half
  Projection Mold 1:
  A second mold half comprising projections was fabricated by IBM Corp., Rochester, Minn. as follows. A total of 24 projections were machined using EDM into one side of a steel plate made of S7 steel having a hardness of 52 on the Rockwell hardness C scale. The dimensions of the steel plate were: 19 mm in length, 19 mm in width, and 47.7 mm in thickness. The projections were arranged in an array with a center projection replaced with an ejector pin. The ejector pin was 63 mils (1.575 mm) in diameter and was used to enable ejection of the resulting molded article. The array of projections covered an area of approximately 0.25 in$^2$ (1.6 cm$^2$). Each projection had a hemisphere-shaped base end and a neck identical in shape to neck 950 in FIG. 9A. The dimensions of the projection were: the maximum diameter of base end was 1.190 mm, the neck was positioned directly on top of the hemisphere and the neck had a drafting angle of 9.6 degrees, diameter of neck at tip end was 0.1 mm resulting in a tip end 980 area of 0.314 mm$^2$, the length of the entire projection was 1.17 mm and the distance between the tips of the projections was about 1.513 mm.

Projection Mold 2:
  A second mold half comprising projections was fabricated by Detail Tool and Engineering, Blaine, Minn. as follows. A total of 25 projections were machined using EDM into one side of a steel plate made of S7 steel having a hardness of 52 on the Rockwell hardness C scale. The dimensions of the steel plate were: 19 mm in length, 19 mm in width, and 47.7 mm in thickness. The projections were arranged in a 5×5 array with the array covering an area of approximately 1.6 cm$^2$. No ejector pin was used. Each projection was shaped as shown in FIG. 3A. The dimensions of the projection were: the maximum diameter of base end 310 was 0.0398 in. (inches) (1.0 mm), the length of base end 310 was 0.0400 in. (1.0 mm), the included angle of base end 310 was 60 degrees, the diameter of neck 320 at base end was 0.006 in. (0.152 mm), the length of neck 320 was 0.0270 in. (0.68 mm), the drafting angle of the neck was 0.5 degrees, contact surface 340 had an area of 0.000013 in$^2$ (8400 µm$^2$), tip end 330 had an area of (4040 µm$^2$), beveled surface 350 had a length of 0.0147 in. (0.37 mm) and an angle of about 8 degrees, and the distance between the tips of the projections was 0.07 in. (1.78 mm).

Materials
  Polycarbonate pellets available from Lexan HPS1R, Sabic Innovative Plastics, Pittsfield Mass. were used. The polycarbonate pellets had the following material characteristics (taken from the literature): 1) a melt flow index of 25 g (gram)/10 min (minute) when measured according to ASTM D1238 at conditions of 300° C. and 1.2 kgf (kilogram-force); 2) a tensile modulus of 2350 MPa (megaPascal) when measured according to ASTM D638 at a rate of 50 mm (millimeter)/min; 3) a tensile stress at yield, Type I of 63 MPa when measured according to ASTM D638 at a rate of 50 mm/min; 4) a tensile elongation at break of 120% when measured according to ASTM D638 at a rate of 50 mm/min; 5) Izod notched impact strength of 12 KJ (kiloJoule)/m according to ISO 180/1 A at 23° C.; 6) a Vicat softening temperature of 139° C. when measured according to ISO 306 at a rate of 120° C./h (hour).

Polypropylene copolymer available from Total Petrochemicals 1751, Houston Tex. was used. The polypropylene copolymer had the following material characteristics (taken from the literature): 1) a melt flow index of 20 g/10 min when measured according to ASTM D1238; 2) a tensile modulus of 434 MPa when measured according to ASTM D638; 3) a tensile elongation at break of >300% when measured according to ASTM D638; and 4) Izod notched impact strength of 587 J/m according to ASTM D256A at 23° C.

Methods
  Method 1:
  Cavity Mold 1 and Projection Mold 1 were installed in a mold base in a 65-ton injection molding machine (Krauss- Maffei KM65-180CX, Krauss-Maffei Technologies GmbH, Munchen, Germany) equipped with a high temperature oil thermalcycling unit (Regloplas 301 DG, Regloplas Corp., St. Joseph, Mich.). As is common in the art, the parting line of the mold assembly had both primary and secondary vents for general air evacuation during injection of the polymeric material. The submicrometer venting between the plates of the stacked laminate mold provided additional venting, which enabled the high fidelity replication of the microstructure. Polycarbonate pellets were loaded into a hopper and subsequently fed into a reciprocating screw to achieve the proper processing temperature in the melt state. Cavity Mold 1 and Projection Mold 1 were heated to a specified temperature (hereafter referred to as the "mold temperature at injection") above the softening point of the polycarbonate. The molding cycle was initiated by closing Cavity Mold 1 with Projection Mold 1. The molds were clamped together with 15 tons of force to form a clamped mold chamber. A first portion (approximately 80-90% of the part size volume) of the total amount of polymeric material from the reciprocating screw was injected into the clamped mold chamber. The first portion of polymeric material was injected into the mold chamber at a fixed velocity (hereafter referred to as the "injection velocity"). After injecting the first portion of the material, the process was switched from an injection velocity driven to a pressure driven process by applying fixed pressure (hereafter referred to as the "pack pressure") to force the remainder of the molten polymeric material into the mold cavity. The pack pressure was applied for a fixed time (hereafter referred to as the "hold time"). The pack pressure was subsequently released and the mold chamber was cooled to an appropriate ejection temperature (hereafter referred to as the "mold temperature at ejection"), which was at or below the softening temperature of the polycarbonate. Details of the injection velocity, pack pressure, hold time, injection temperature, and ejection temperature used for each example are given in Table 1.

Method 2:

The method as described in Method 1 was used with the following exceptions: the polymeric material was polypropylene copolymer and Cavity Mold 2 and Projection Mold 2 were used. The following molding parameters were used: injection velocity of 2.54 cm/sec, pack pressure of 41.4 MPa, hold time of 4 sec, mold temperature at injection of 49° C., and a mold temperature at ejection of 49° C.

Hollow Microneedle Arrays

Examples 1-10

Method 1 was used with the injection velocity, pack pressure, hold time, mold temperature at injection, and mold temperature at ejection as listed in Table 1. The resulting hollow microneedle height and average orifice width for each example is also shown in Table 1. Hollow microneedle height and size of molded hollow features were measured via stereomicroscopy and scanning electron microscopy. The hollow microneedle height and orifice width was taken as the average of nine measurements (three from each individual array).

TABLE 1

| Example Number | Injection Velocity [inches/sec, (cm/sec)] | Pack Pressure [psi, (MPa)] | Hold Time [sec] | Mold temperature at injection [° F., (° C.)] | Mold temperature at ejection [° F., (° C.)] | Average needle height [μm] | Average orifice width [μm] |
|---|---|---|---|---|---|---|---|
| 1 | 0.70 (1.78) | 12000 (82.7) | 10 | 335 (168.3) | 270 (132.2) | 502 | 25 |
| 2 | 0.70 (1.78) | 12000 (82.7) | 6 | 335 (168.3) | 270 (132.2) | 495 | 25 |
| 3 | 0.70 (1.78) | 12000 (82.7) | 4 | 335 (168.3) | 270 (132.2) | 489 | 25 |
| 4 | 0.70 (1.78) | 10000 (68.9) | 4 | 335 (168.3) | 270 (132.2) | 485 | 25 |
| 5 | 0.70 (1.78) | 14000 (96.5) | 4 | 335 (168.3) | 270 (132.2) | 495 | 25 |
| 6 | 0.70 (1.78) | 14000 (96.5) | 8 | 335 (168.3) | 270 (132.2) | 501 | 25 |
| 7 | 0.50 (1.27) | 14000 (96.5) | 8 | 335 (168.3) | 270 (132.2) | 499 | 25 |
| 8 | 0.50 (1.27) | 12000 (82.7) | 8 | 335 (168.3) | 270 (132.2) | 498 | 25 |
| 9 | 1.00 (2.54) | 12000 (82.7) | 8 | 335 (168.3) | 270 (132.2) | 500 | 25 |
| 10 | 0.70 (1.78) | 12000 (82.7) | 8 | 335 (168.3) | 270 (132.2) | 500 | 25 |

Examples 1-10 illustrate injection molding of hollow microneedle arrays using polycarbonate in combination with stacked laminate tooling. Although not wanting to be limited by theory, it is believed that the ability to use lower mold temperatures at injection, is due to the enhanced venting in the needle direction enabled by the submicrometer venting. The lower mold temperatures used at injection allow for a reduction in cycle time and an increase in hollow microneedle feature fidelity. However, the fidelity of the hollow microneedles may be compromised by using non-optimized conditions as is known in the art. For example, if a mold temperature at injection is too high, the height of the hollow microneedle increases (e.g., mold temperature at injection 176.7° C., average height of 512 μm) due to the molten polymeric material entering unwanted areas of the mold assembly and the insufficient quenching of the molten polymer prior to ejection. Conversely, a mold temperature at injection set too low will cause incomplete fill of the microneedle cavity (e.g., mold temperature at injection 132.2° C., average height of 93 μm). Thus, mold temperature at injection and mold temperature at ejection may be important factors to consider to ensure high fidelity of the resulting molded article.

The combined data for Examples 1-10 indicated that the hollow microneedle arrays had an average hollow microneedle height of 494 μm (+/−5 μm) and an average tip length of 1 to 2 μm (+/−1 μm) in the shortest dimension.

Comparison between cavity shape and the resulting molded article from Examples 1-10 showed part-to-part reproducibility of 98.7%. This value suggests that 1.3% of the cavity was not fully replicated in the polymeric material. Measurements were taken as the average of nine measurements (three from each individual array) and evaluated the hollow microneedle base diameter versus the cavity base width, the orifice area versus the contact area, the hollow microneedle height versus the cavity length, and the hollow microneedle tip diameter versus the cavity tip diameter.

Figure 10B:
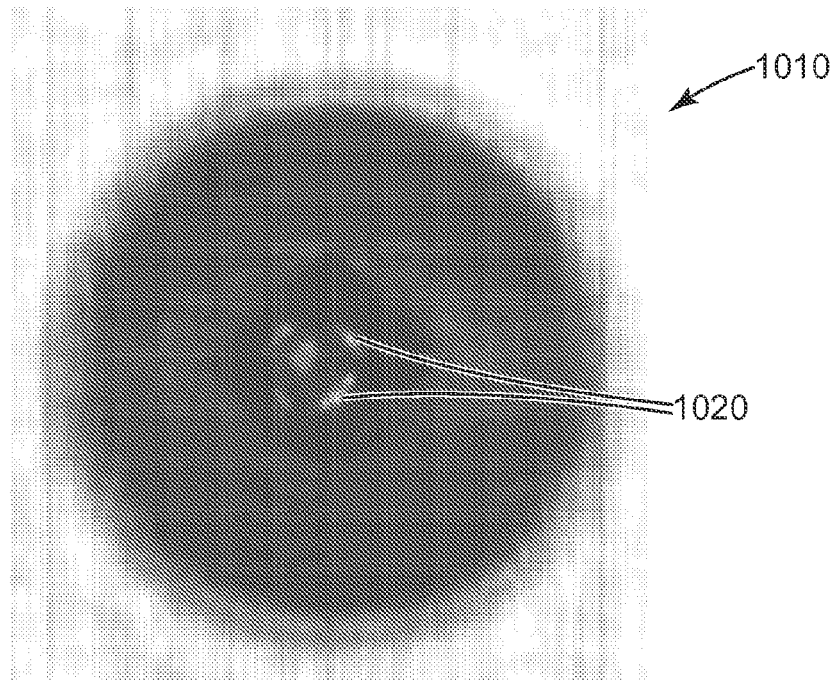
FIG. 10B is an enlarged view of hollow microneedle 1010 from hollow microneedle array 1000.
Figure 10C:
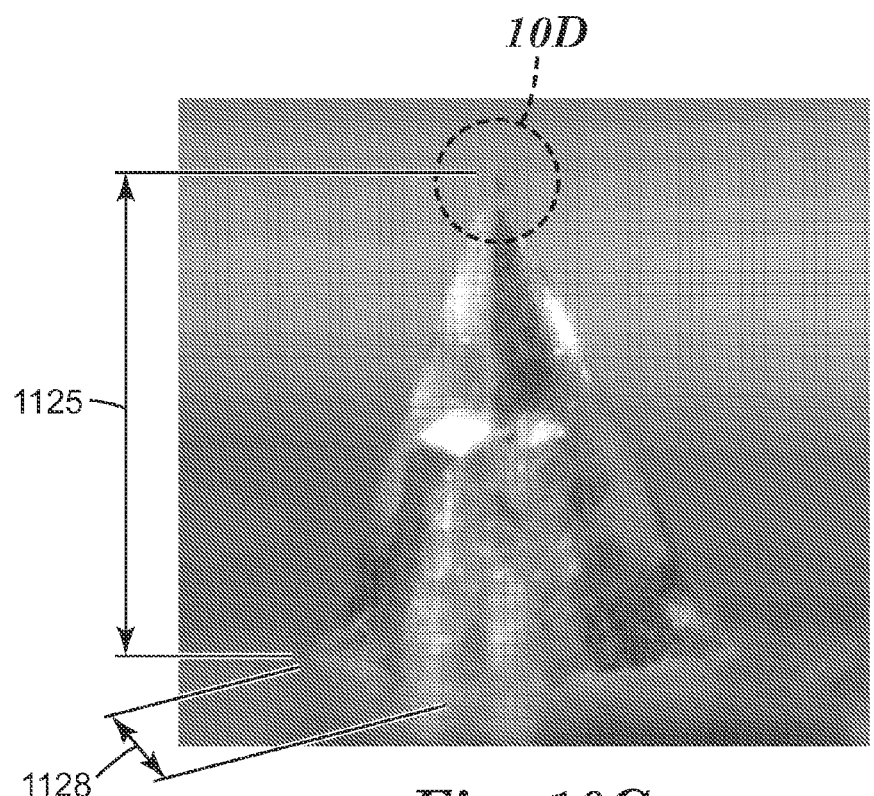
FIG. 10C is a side-view picture of a hollow microneedle according to Example 6.
Figure 10D:
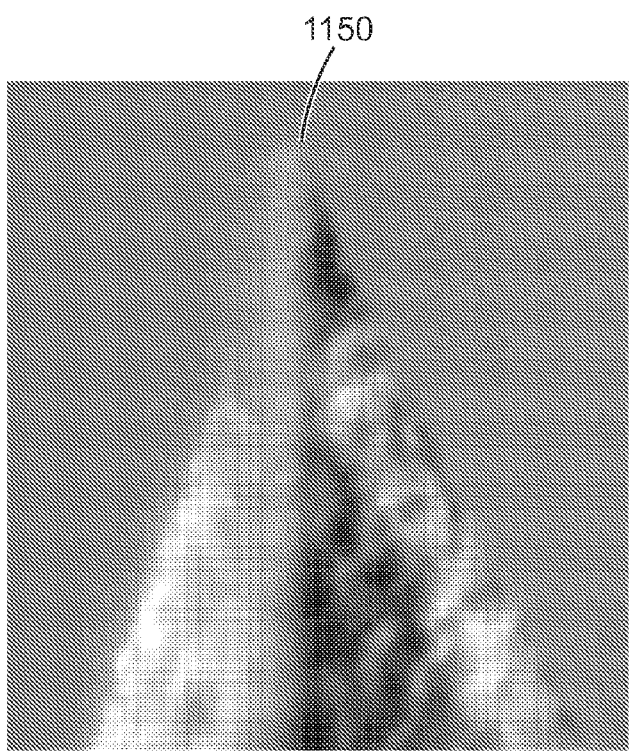
FIG. 10D is an enlarged view of the tip of the hollow microneedle of FIG. 10C.

The hollow microneedle array of Example 6 was viewed under an optical microscope, (Olympus SZX12, Olympus America Inc., Center Valley, Pa.). Shown in FIG. 10A is a picture of hollow microneedle array from Example 6. Hollow microneedle array 1000 comprises a plurality of hollow microneedles 1010. Shown in FIG. 10B is an enlarged view of one hollow microneedle 1010. Four orifices (two of the orifices labeled 1020) are shown on hollow microneedle 1010. FIG. 10C is a side-view of one hollow microneedle, where 1125 depicts the height of the hollow microneedle and 1128 depicts the edge base width of the hollow microneedle. FIG. 10D is an enlarged view of the tip of one hollow microneedle viewed at 3,456× magnification. Tip 1150 of the hollow microneedle was measured as approximately 1 µm. Tip dimensions of 800 nm to 5 µm were observed on the hollow microneedle array 1000. The hollow microneedle had four side ports (one on each wall), 150 µm away from the apex. The size of the orifice made on the hollow microneedle was 25 µm in width. Each orifice was in fluid communication with the bore, which had a width dimension of 130 µm near its apex and a width dimension of 1000 µm at the base of the hollow microneedle.

Example 11

Molded hollow microneedle arrays were prepared according to the procedure described in Method 1 with the following exception. The stacked laminate mold was maintained at 10° C. lower mold temperature at injection relative to the plurality of projections. This ensured a proper ratio of thermal expansion of both mold materials to achieve uniform load of the projections against the cavities. Over 1000 molding cycles were made using the mold halves. Inspection of the resulting molded articles showed uniform hollow microneedle height and orifice area on each of the hollow microneedles across the arrays. Also, no indication of wear on the projection mold half or the cavity mold half was observed.

Example 12

Figure 11A:
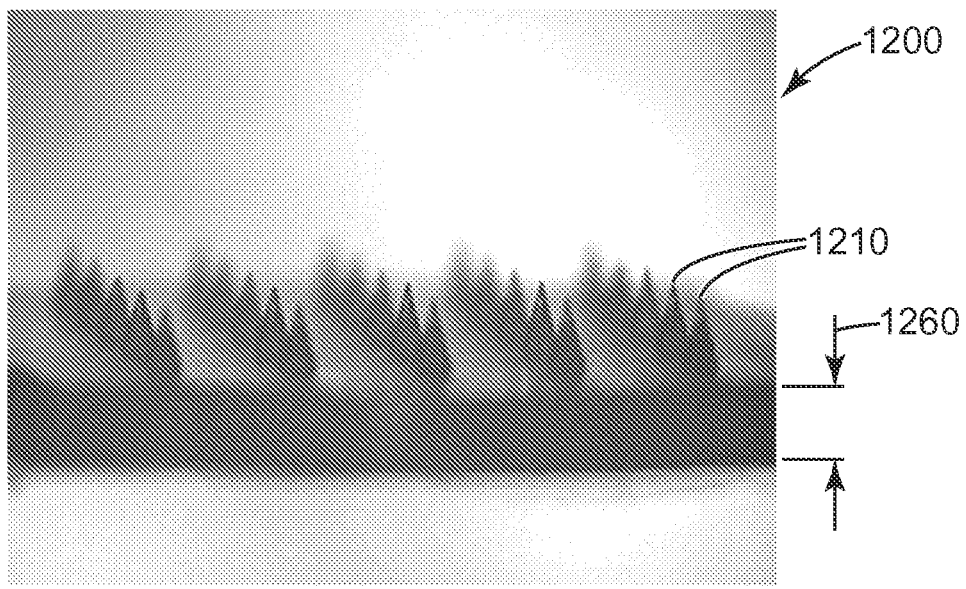
FIG. 11A is a side-view picture of hollow microneedle array 1200 from Example 12.
Figure 11B:
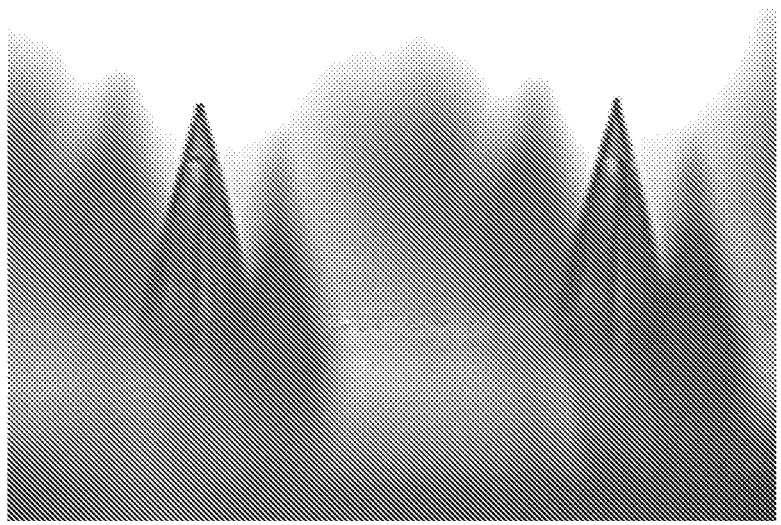
FIG. 11B is an enlarged view of two hollow microneedles from FIG. 11A.

Molded hollow microneedle arrays were prepared according to Method 2. The resulting molded article is shown in FIG. 11A, where the hollow microneedle array 1200, comprised hollow microneedles 1210 in a 5×5 array and had a resulting molded article support base thickness 1260. FIG. 11B is an enlarged view of two microneedles. The hollow microneedles had an average height of 895 µm and comprised two orifices on opposed sides of the hollow microneedle; each orifice had an average area of approximately 8600 µm$^2$.

The present disclosure has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the disclosure. Thus, the scope of the disclosure should not be limited to the exact details of the compositions and structures described herein, but rather by the language of the claims that follow.

What is claimed is:

1. A method of manufacturing a hollow microneedle array comprising:
   (a) providing a first mold half comprising a stacked laminate mold, the stacked laminate mold comprising a plurality of plates and a plurality of cavities, wherein each of the plates comprises:
      (i) opposed first and second major surfaces; and
      (ii) a first mold surface connecting said first and second major surfaces; and wherein the plurality of cavities is open at least to the first mold surface and includes a cavity surface wherein the cavity surface intersects each respective plate's first major surface and each respective plate's first mold surface;
   (b) providing a second mold half comprising a second mold surface, wherein the second mold surface comprises a plurality of projections;
   (c) contacting at least the first mold surface or the second mold surface with polymeric material; and
   (d) inserting the plurality of projections into the plurality of cavities.

2. The method of claim 1, wherein the plurality of projections is inserted into the plurality of cavities before contacting at least the first mold surface or the second mold surface with polymeric material.

3. The method of claim 1, wherein at least the first mold surface or the second mold surface is contacted with polymeric material before inserting the plurality of projections into the plurality of cavities.

4. The method of claim 1, wherein the projection comprises a base end, which is connected through a neck to a tip end, wherein the maximum base end area is at least 3 times larger than the tip end.

5. The method of claim 4, further comprising positioning the tip end and at least a portion of the neck within the cavity.

6. The method of claim 1, further comprising registering the plurality of projections into the plurality of cavities.

7. The method of claim 4, further comprising contacting the tip end to at least one surface of the cavity.

8. The method of claim 1, wherein the cavity has a cavity aspect ratio (cavity length to cavity base width) of at least 1.5 to 1.

9. The method of claim 1, further comprising providing venting of the plurality of cavities by a submicrometer spacing between the plurality of plates.

10. The method of claim 9 wherein the submicrometer spacing is provided by the surface roughness of each respective plate's first major surface and second major surface.

11. The method of claim 10, wherein the surface roughness is less than 30 RMS (root mean square) pinch (0.762 RMS µm).

12. The method of claim 1, wherein the cavity surface and the projection comprise different materials.

13. The method of claim 1, wherein the cavity surface comprises a first material and the projection comprises a second material, wherein the first material has a specific modulus that is at least 20 GPa higher than the specific modulus of the second material.

* * * * *